(12) United States Patent
Summit et al.

(10) Patent No.: US 8,613,716 B2
(45) Date of Patent: Dec. 24, 2013

(54) CUSTOM BRACES, CASTS AND DEVICES HAVING LIMITED FLEXIBILITY AND METHODS FOR DESIGNING AND FABRICATING

(75) Inventors: Scott Summit, San Francisco, CA (US); Kenneth B Trauner, San Francisco, CA (US)

(73) Assignee: 3D Systems, Inc., Rock Hill, SC (US)

( * ) Notice: Subject to any disclaimer, the term of this patent is extended or adjusted under 35 U.S.C. 154(b) by 321 days.

(21) Appl. No.: 12/823,626

(22) Filed: Jun. 25, 2010

(65) Prior Publication Data

US 2010/0268138 A1    Oct. 21, 2010

Related U.S. Application Data

(63) Continuation-in-part of application No. 12/615,196, filed on Nov. 9, 2009, now Pat. No. 8,005,651.

(60) Provisional application No. 61/112,751, filed on Nov. 9, 2008, provisional application No. 61/168,183, filed on Apr. 9, 2009, provisional application No. 61/185,781, filed on Jun. 10, 2009, provisional application No. 61/244,749, filed on Sep. 22, 2009.

(51) Int. Cl.
*A61F 5/00* (2006.01)

(52) U.S. Cl.
USPC .......................................................... 602/19

(58) Field of Classification Search
USPC ............ 602/5, 12, 14, 17, 18, 19, 20, 21, 23, 602/26, 27; 128/869, 870, 874, 875; D24/190–192
See application file for complete search history.

(56) References Cited

U.S. PATENT DOCUMENTS

| | | | | |
|---|---|---|---|---|
| 2,318,864 | A | * | 5/1943 | Jackson ........................ 602/21 |
| 2,980,110 | A | * | 4/1961 | Brumfield et al. ............. 602/5 |
| 3,953,900 | A | | 5/1976 | Thompson |
| 4,776,327 | A | * | 10/1988 | Russell ........................ 602/5 |
| 4,807,605 | A | | 2/1989 | Mattingly ..................... 128/75 |
| 4,827,916 | A | | 5/1989 | Kosova |
| 5,443,510 | A | | 8/1995 | Shetty et al. |
| 5,662,594 | A | | 9/1997 | Rosenblatt |
| 5,741,215 | A | | 4/1998 | D'Urso |
| 5,768,134 | A | * | 6/1998 | Swaelens et al. ............ 700/121 |
| 5,857,987 | A | * | 1/1999 | Habermeyer .................. 602/23 |
| 5,880,964 | A | | 3/1999 | Schall et al. |
| 5,888,216 | A | | 3/1999 | Haberman |
| 6,427,695 | B1 | * | 8/2002 | Zanetti et al. ................ 128/846 |
| 6,540,708 | B1 | | 4/2003 | Manspeizer |

(Continued)

OTHER PUBLICATIONS

"International Search Report", mailed Oct. 28, 2011, PCT/US11/41515.

(Continued)

*Primary Examiner* — Patricia Bianco
*Assistant Examiner* — Raymond E Harris
(74) *Attorney, Agent, or Firm* — Paul Tomita

(57) ABSTRACT

A custom device and method for fabricating the custom device includes marking a body with reference points and/or other indicators. Multiple images of the body from multiple angles are then obtained. The images are used to determine the contours of the body and the other markings are located and used to design the custom device. The custom device can be fabricated as a single piece structure or in multiple pieces that are assembled to complete the custom device.

18 Claims, 18 Drawing Sheets

(56) References Cited

U.S. PATENT DOCUMENTS

| | | |
|---|---|---|
| 6,572,571 B2 | 6/2003 | Lowe |
| 6,597,965 B2 | 7/2003 | Graves et al. |
| 6,613,006 B1 * | 9/2003 | Asherman .................. 602/5 |
| 6,725,118 B1 | 4/2004 | Fried et al. |
| 6,726,641 B2 * | 4/2004 | Chiang et al. ............... 602/5 |
| 6,968,246 B2 | 11/2005 | Watson et al. |
| 7,127,101 B2 * | 10/2006 | Littlefield et al. ......... 382/154 |
| 7,210,926 B2 * | 5/2007 | Tadros et al. ................. 433/6 |
| 7,242,798 B2 * | 7/2007 | Littlefield et al. ......... 382/154 |
| 7,340,316 B2 | 3/2008 | Spaeth et al. |
| 7,896,827 B2 * | 3/2011 | Ingimundarson et al. ...... 602/26 |
| 8,005,651 B2 | 8/2011 | Summit et al. |
| 2002/0016631 A1 | 2/2002 | Marchitto et al. |
| 2003/0032906 A1 | 2/2003 | Narula et al. |
| 2003/0065259 A1 * | 4/2003 | Gateno et al. ............... 600/425 |
| 2004/0019266 A1 | 1/2004 | Marciante et al. |
| 2004/0068337 A1 | 4/2004 | Watson et al. |
| 2004/0162511 A1 | 8/2004 | Barberio |
| 2004/0230149 A1 | 11/2004 | Littlefield et al. ............ 602/17 |
| 2004/0236424 A1 | 11/2004 | Berez et al. |
| 2004/0260402 A1 | 12/2004 | Baldini et al. |
| 2005/0015172 A1 * | 1/2005 | Fried et al. .................. 700/118 |
| 2005/0043835 A1 | 2/2005 | Christensen |
| 2005/0061332 A1 * | 3/2005 | Greenawalt et al. ......... 128/882 |
| 2005/0065458 A1 * | 3/2005 | Kim ............................. 602/5 |
| 2006/0161267 A1 | 7/2006 | Clausen |
| 2007/0225630 A1 | 9/2007 | Wyatt et al. |
| 2008/0120756 A1 | 5/2008 | Shepherd |
| 2008/0294083 A1 * | 11/2008 | Chang et al. ................ 602/28 |
| 2008/0319362 A1 | 12/2008 | Joseph |
| 2009/0254015 A1 | 10/2009 | Segal et al. ................. 602/19 |
| 2010/0137770 A1 * | 6/2010 | Ingimundarson et al. ...... 602/27 |
| 2010/0138193 A1 | 6/2010 | Summit et al. ............... 703/1 |

OTHER PUBLICATIONS

English Translation of China's First Office Action for Chinese Application No. 200980144730.6 dated Nov. 28, 2012, (16 pages).

International Search Report and Written Opinion, PCT Application No. PCT/US2010/055793, International Filing Date: Nov. 8, 2010.

* cited by examiner

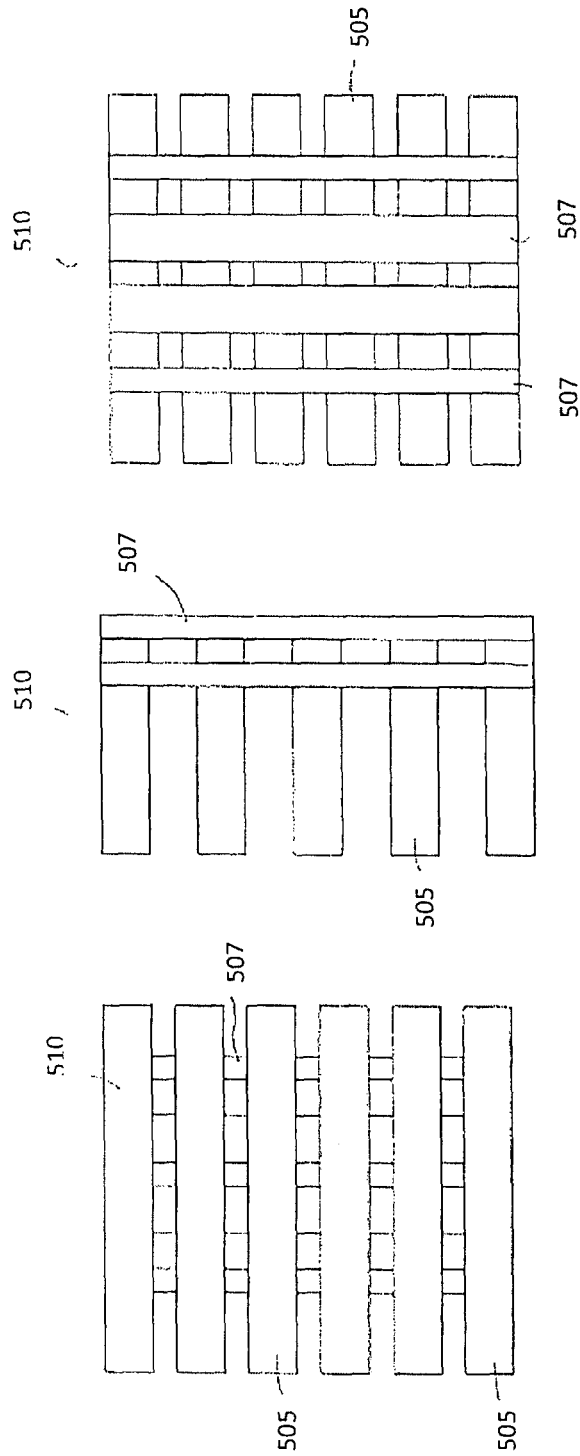

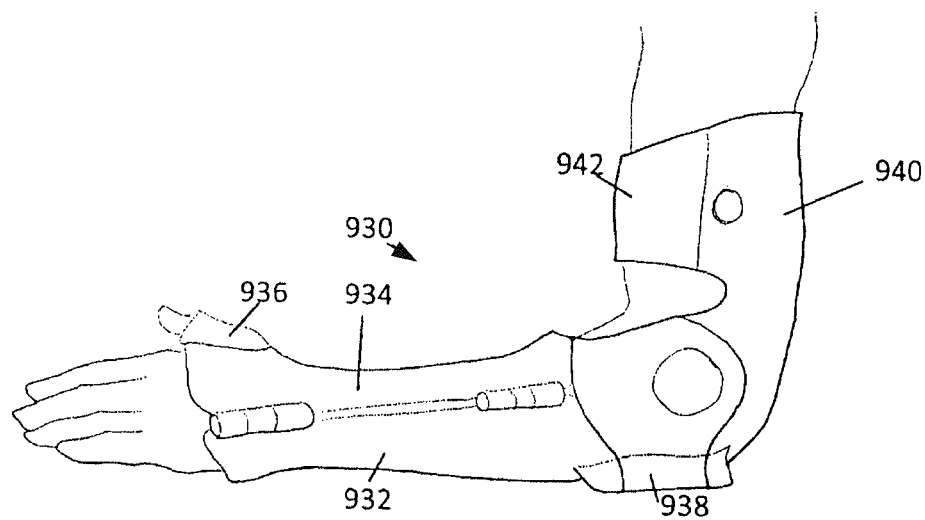
FIG. 32
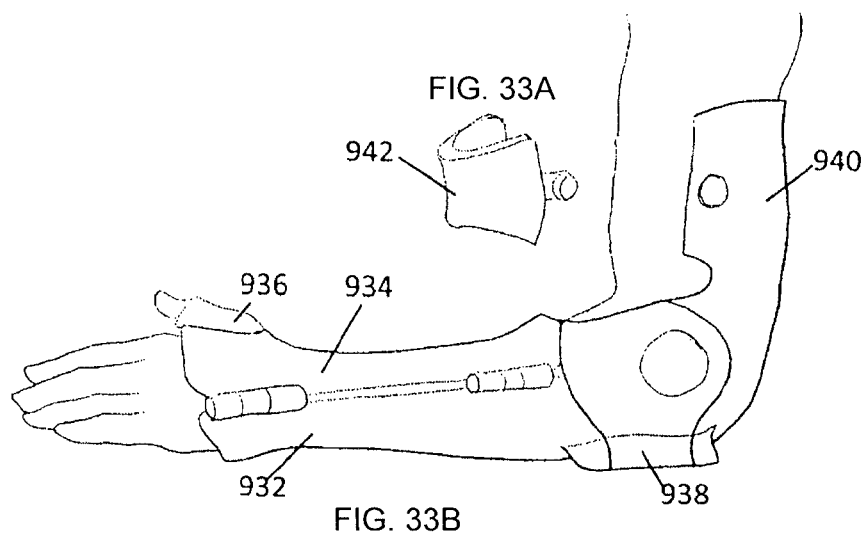
FIG. 33A
FIG. 33B
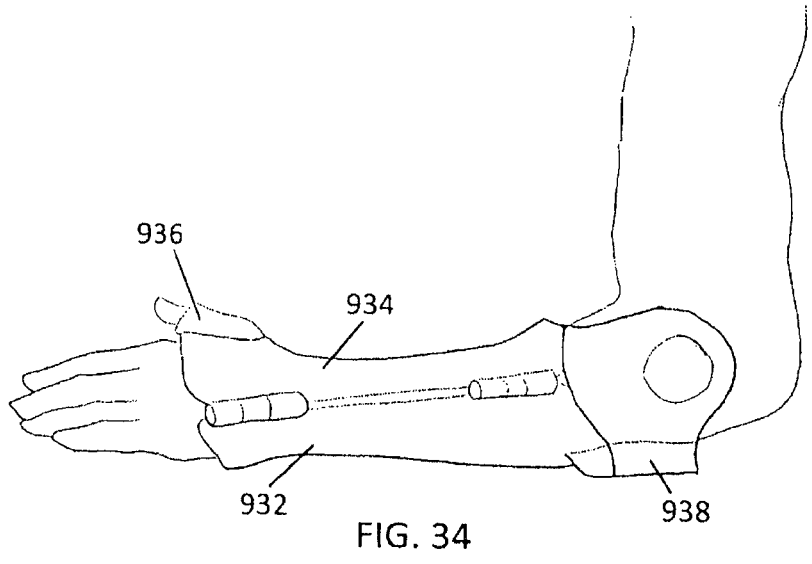
FIG. 34

CUSTOM BRACES, CASTS AND DEVICES HAVING LIMITED FLEXIBILITY AND METHODS FOR DESIGNING AND FABRICATING

CROSS REFERENCE TO RELATED PATENT APPLICATIONS

This patent application is a continuation-in-part of U.S. patent application Ser. No. 12/615,196, "CUSTOM BRACES, CASTS AND DEVICES AND METHODS FOR DESIGNING AND FABRICATING" filed Nov. 9, 2009 now U.S. Pat. No. 8,005,651, which claims priority to U.S. Provisional Patent Application No. 61/112,751, "BRACE AND CAST" filed on Nov. 9, 2008, U.S. Provisional Patent Application No. 61/168,183, "ORTHOPEDIC BRACES" filed in Apr. 9, 2009, U.S. Provisional Patent Application No. 61/185,781, "BESPOKE FRACTURE BRACE" filed in Jun. 10, 2009, and Provisional Patent Application No. 61/244,749, "BESPOKE SCOLIOTIC BRACE" filed Sep. 22, 2009, which are hereby incorporated by reference.

BACKGROUND

There are various types of braces and casts that are used to protect a portion of a body during recovery. Braces are used to limit the movement of a joint and are useful in preventing injury or allowing a joint to heal by preventing movement correlating with the injury. Common braces are elastic which are made of stretch materials or hinged which include some hard components. Elastic braces are frequently made from woven materials such as cotton, Lycra, nylon or other blends that provide exceptional breathability and wearing comfort. These braces conform to the elbow, wrist, leg and knee providing a natural freedom of movement. Braces are typically off the shelf items that are secured to the patient's body with straps. The brace can have pads or other cushioning which are placed between the patient's body and the more rigid brace structures. Flexible off the shelf braces offer inexpensive modalities for restriction of motion and added support of targeted body parts. However, the use of flexible materials and generic sizing limits the amount of control that the off the shelf brace can provide. For a given individual the "off the shelf" braces offer limited conformability. The axis of rotation is not accurately placed relative to the native joint axes and is less useful for clinical range of motion bracing situations that demand greater accuracy in position, conformation, and control of motion.

Hinged braces usually offer greater support and stability than elastic or neoprene braces. Hinged braces are a subset of range of motion braces. For the rehabilitation or treatment of many diarthrodial joints such as the knee, and elbow, motion is required early after injury, surgery or treatment to achieve a good clinical and functional result. Motion braces provide support to the injured joints while allowing for controlled motion in the proper planes with restriction of motion established by the health care provider. Without early motion, stiffness results with reduction in the long term range of motion and suboptimal clinical results. Hinged knee braces are examples of dynamic braces that move in order to provide increased support of knee joints following an injury or after surgery. Hinged knee braces are used for treatment of ligamentous injuries within the knee or on a perioperative basis. They are most frequently used for the treatment of anterior cruciate ligament injuries and medial collateral ligament injury in the knee. These braces are also used in a protective basis by athletes post injury and on a prophylactic basis such as football linemen, who wear the braces on a routine basis for protection. Rehabilitative removable knee braces are also available as range of motion braces. These braces have hinges incorporated into the brace that can specify and limit the degrees of motion in both flexion and extension. These can also be locked into full extension with a "drop lock" mechanism. These range of motion braces are used frequently in a trauma or reconstructive setting in which the range of motion must be advanced in a controlled setting. Other dynamic splints offer additional stress applied to the joint to achieve increased motion in the setting of joint contractures. These braces apply and additional force at the extremes of motion to assist in stretching out the joint.

In contrast to a brace or a splint, a cast is typically a circumferential device used to immobilize and protect a limb or body part. An orthopedic cast is a circumferential shell, frequently made from plaster or fiberglass, encasing a limb or, in some cases, large portions of the body to hold a broken bone or bones in place to allow healing. Upper extremity casts are those which encase the arm, wrist, and/or hand. A long arm cast encases the arm from the hand to about 2 inches below the arm pit, leaving the fingers and thumbs free. A short arm cast, in contrast, stops just below the elbow. Both varieties may, depending on the injury and the doctor's decision, include one or more fingers or the thumb, in which case it is called a finger spica or thumb spica cast. Lower extremity casts are classified similarly, with a cast encasing both the foot and the leg to the thigh being called a long leg cast, while one covering only the foot and the lower leg below the knee is called a short leg cast. A walking heel may be applied, or a canvas, leather or rubber cast shoe provided to the patient who is expected to walk on the immobilized limb during convelescence (referred to as being weight bearing). Where the patient is not to walk on the injured limb, crutches or a wheelchair may be provided. The sole of a leg cast may also be extended to the tip of the toes, if providing a toeplate. This addition may be made to offer support to and stabilize the metatarsals and to protect the toes from additional trauma. This is a common treatment for a broken foot. In some cases, a cast may include the upper and lower arm and the elbow, but leaves the wrist and hand free, or the upper and lower leg and the knee, leaving the foot and ankle free. Such a cast may be called a cylinder cast, or may simply be called a long arm or long leg cast.

Orthopedics casts are typically single use, non removable devices that are circumferentially applied to the patient and are not intended to be removed by the patient. Typically, any removal of the cast disrupts the conformity of the underlying cotton layer and leads to the replacement of the device. Immobilization devices in which the structural components are non circumferential are referred to as splints. These typically apply rigidity to a portion of the body part but allow motion, expansion or adjustment in other planes.

Casts are typically applied by physician or cast technician in layers. The body part which will receive the cast is initially covered with a thin woven cotton layer or stockinette. The part is then overwrapped with thin loose cotton wrap such as Webril that is applied in layers. An attempt is made to apply the cotton as uniformly as possible as any folds or imperfection can be a source of future skin breakdown once the hard outer shell is applied. Typically greater amounts of the cotton padding layer are applied over the terminal regions for the cast. Bony prominences also receive additional padding. Once the padding is applied, the body part is wrapped in either plaster of fiberglass. These materials are self setting and are activated by immersing in water prior to wrapping around the body part. Casts are circumferential devices and the plaster/fiberglass is applied as a wrap around the body part. The physician then applies a mold to the cast in an attempt to make the cast conform and support the body part in the critical planes. For example in the treatment of a fracture, typically a 3 point mold is applied in the plane of likely collapse or deformation of the fracture, to prevent displacement. As the cast is circumferential, hoop stresses tend to expand the cast dimensions in the planes orthogonal to the mold. Control of the casting depends on the skill of the practitioner, the amount of padding applied, the amount of tension on the materials and the appropriate molding of the cast during the setting process. Once the cast has set, the cast may be trimmed and additional padding may be applied to the edges if necessary to address sharp edges.

Imperfect application of the cast is associated with multiple complications including skin breakdown, discomfort, emergency room visits, compartment syndromes, loss of fixation or fracture reduction, malunion of fractures, need for surgical intervention, nerve injury, vascular injury. Revision of casts with removal and application of new casts is a frequent occurrence and is associated with significant cost and patient morbidity.

Body casts, which cover the trunk of the body and in some cases the neck up to or including the head or one or more limbs, are rarely used today for adults, but continue to be used commonly for the treatment of pediatric conditions. A body cast encases the trunk of the patient's body, and may have sections that extend over the shoulders. The body cast is usually referred to as a body jacket. A cast which includes the trunk of the body and one or more limbs and a cast which includes the "trunk" of the arm and one or more fingers or the thumb are called a spica cast. For example, a shoulder spica cast includes the trunk of the body and one arm, usually to the wrist or hand. Shoulder spica casts are used less frequently today, having been replaced with specialized splints and slings which allow early mobility of the injury so as to avoid joint stiffness after healing. A hip spica cast includes the trunk of the body and one or more legs. A hip spica cast which covers only one leg to the ankle or foot may be referred to as a single hip spica, while one which covers both legs is called a double hip spica. A one-and-a-half hip spica cast encases one leg to the ankle or foot and the other to just above the knee. The extent to which the hip spica covers the trunk depends greatly on the injury and the surgeon. For example, the spica cast may extend only to the navel, allowing mobility of the spine and the possibility of walking with the aid of crutches, or it may extend to the rib cage or even to the armpits in some rare cases. Hip spica casts were formerly common in reducing femoral fractures, but today they are used commonly for the treatment of pediatric hip conditions. In some cases, a hip spica cast may only extend down one or more legs to above the knee. Such casts, called pantaloon casts, are used to immobilize an injured lumbar spine or pelvis, in which case the trunk portion of the cast usually extends to the armpits.

Body casts are typically applied with use of a special frame and the use of multiple technicians or physicians. The patients may require sedation if adults. Body casts or hip spica casts applied to pediatric patients usually require general anesthesia and the casts are applied in the operating room. The body and hip spica casts are typically worn for extended duration of 6 to 12 weeks. Excessive cost and morbidity is associated with the need to replace the device. Hygiene is a difficult problem for pediatric spica casts as soilage of the brace is a frequent occurrence. The need for a general anesthetic to replace the cast is a strong disincentive to change the cast for anything other than a medical reason.

Other body casts which were used to protect an injured spine or as part of the treatment for a spinal deformity such as scoliosis include the Minerva cast and Risser cast. The Minerva cast includes the trunk of the body (sometimes extending down only so far as the rib cage) as well as the patient's head, with openings provided for the patient's face, ears, and usually the top of the head and hair. The Risser cast was similar, extending from the patient's hips to the neck and sometimes including part of the head.

Casts are frequently made from plaster, encasing the limb and/or body. Plaster bandages consist of a cotton bandage that has been impregnated with plaster of paris, which hardens after it has been made wet. Alternatively, bandages made of synthetic materials are often used in casts. For example, casts are often made of knitted fiberglass bandages impregnated with polyurethane, sometimes bandages of thermoplastic. These synthetic material casts are lighter and dry much faster than plaster casts.

Because the casts are applied directly to the patient's body, they have a custom fit. In contrast, most braces for common medical injuries or conditions are off the shelf items that are adjusted to fit the patient. For more severe injuries, chronic conditions or perioperative immobilization, greater brace control and conformity is required. These patients require the use of custom braces that are frequently produced by specialists such as prosthetists and orthotists. These specialists typically either take a mold of the patient from which they can produce a positive model of the patient. Around this positive mold, the prosthetist can then wrap materials and construct a custom device. The amounts of padding and reinforcement are based on the clinical experience of the orthotist and the "art" of brace manufacturing. When custom prosthetics, braces and orthotics are designed, medical practitioners frequently rely on their hands to feel the patient's soft tissue and bone structure. The practitioners identify bony protuberances that they feel under the tissue and mark these locations as landmarks reference points that they can then use to create the custom device for the body. The practitioners work on an iterative basis with the patient and the models of the patient to create a brace that conforms to the patient yet has the proper padding and support necessary for its clinical use.

There are many limitations to the traditional methods of brace production. The entire process is very labor intensive and inefficient. The limitations of the method of sizing and manufacture have limited the end product. Manufacturing restrictions have limited the choice of designs, and the functionality of the end product. The custom devices are labor intensive and they are limited in geometric complexity. The custom devices can also be highly inaccurate since they are hand made and may only vaguely represents the patient's body. The hand made process also does not allow for special adjustments to the custom device, which may include clearances, or custom windows for tender spots, rashes, birthmarks, moles, nipples, stitches, bruises, or other areas on the skin that may require special clearance or avoidance. What is needed is an improved system and method for designing braces that are more accurately fitted to the patient, thinner, stronger, more comfortable and selectively flexible.

SUMMARY OF THE INVENTION

The present invention is directed towards a process for fabricating a custom brace, cast or device based upon scan data from a patient. In a preferred embodiment a photogrammetry process is used in which the surface data for a patient is obtained from a plurality of photographs of the patient. In order to accurately measure the surface of the patient, reference points can be applied to the patient's skin in various different ways. The surface should have at least twelve well distributed reference points visible in each photograph and at least twenty reference points for an entire surface of an object. More reference points will result in a more accurate measurement of the object. The marks can be dots formed by ink, stickers, or other markings placed directly on the patient or on a form fitting cover such as a stockinette worn by the patient. In an embodiment, the cloth of the form fitting covering can be printed with the dots, textured pads or a grid of intersecting lines so that the patient will have a set of reference points as soon as the covering is worn by the patient. In yet another embodiment, a light projector can be used to project a pattern of light onto the patient. The pattern of light can be an array of spot points, a grid of intersecting lines or any other pattern that allows images of points on the patient to be detected. The light on the patient serves as the markings can be white or colored light markers that are projected onto the patient with a projector. Multiple projectors or mirrors may be necessary to project the light onto all required surfaces of the patient.

In addition to reference points for obtaining the surface contours of the patient's body surface, the doctor or practitioner can also mark areas of the patient's body to indicate the location of other features of the brace. For example, markings can indicate the end edge(s) of the brace, padding areas, boney prominences, sensitive areas of the skin, holes, windows, pathologic sites (fracture or surgical site localization), underlying anatomy (ex spinous processes and spine alignment) recessed areas where the brace should not be made precisely to the contour of the patient and other features to be formed in the brace. The markings can be made directly on the patient or on the form fitting cover worn by the patient. Like the reference points, the additional markings must provide a clear visual contrast. The markings can be coded by color or in another manner to indicate the type of feature to be formed at the markings. The different codings can also be used to indicate the degree or amount of deformation in an identified region, type of window, or other brace feature. The markings can be a three dimensional object(s) that provide additional information. For example, a rod, an arrow or other object marker can indicate an axis of rotation of a joint or other features.

After the patient has been marked, the portion of the patient's body that is in need of a cast or brace is placed in front of one or more still or video cameras. The cameras can face one or more sides of the patient's body and can be spaced apart from each other by a known distance. In some embodiments, a set of cameras can be arranged around the patient so that a complete set of still images or photographs of the body around a circumference can be taken. In a preferred embodiment, the cameras are arranged in groups of two cameras. The two cameras can be mounted on a bracket that spaces the cameras apart from each other. The two cameras are aimed in the same general direction towards the patient or limb of the patient but offset by an angle. In a preferred embodiment, the camera lenses can be parallel to each other in a first plane and angled towards each other in a second plane. The separation and angle allow the two cameras to each take a picture that includes the same portions of the patient's body but from slightly different angles. The reference points on the body are triangulated from the pictures to obtain the surface contours. If photographs around the entire patient are needed, three or four groups of cameras can be arranged around and directed towards the patient. The cameras can be coupled to a single switch which causes all of the cameras to be actuated simultaneously. The cameras can also be coupled to a flash mechanism. The flash for one camera can be triggered by the shutter of one camera being actuated. The other cameras aimed at the patient can include light sensors cause their shutters to actuate in response to the flash of light. Thus, the actuation of the first camera will immediately cause all other cameras to be actuated. Since all pictures are taken in a fraction of a second, the body can be placed in front or between the cameras and there is normally no need to immobilize the patient or hold the body or limb still for an extended period of time.

This fast image capture feature is particularly important for pediatric or veterinary medical devices such as pediatric spica casts or veterinary braces. It can be very difficult to keep an infant or an animal steady for other types of scanning processes. For most children and animals casting and bracing is a traumatic experience associated with significant pain and morbidity. Both application and removal of casts and braces is associated with discomfort. For many applications the children and animals require either sedation or anesthesia for application of the casts. For example hip spica casts most frequently are applied with the patient in an induced sleep in the operating room.

Capturing a three dimensional image of a child's anatomy requires that the child be held immobile during the duration of the scan. Otherwise the child would require sedation. For most pediatric applications, only photogrammetry will offer near instantaneous three dimensional image capture. Combining with markings and photogrammetry, children can undergo virtual fittings for braces while minimizing the need for sedation or anesthesia and reducing the trauma of the experience. Because many infants have a substantial amount of baby fat, the marking of the infant may be the most efficient means for identifying the locations of the underlying anatomy. Common applications for this technology include but are not limited to: pediatric spica casts, Pavlik brace, clubfoot casting, metartus adductus casting, Blounts disease casting/bracing, ankle foot orthosis, pediatric ankle casts, pediatric walking casts, spine-TLSO braces, halo body cast, cervical collar, torticollis bracing and other medical devices. By obtaining data from images, there is no need to keep the infant or animal still for an extended period of time.

In another embodiment, a single 3-D camera can simultaneously capture multiple off axis images via a single camera. The single camera may capture multiple images on a single frame of film. The multiple images can be used to capture the 3-D image. It is also possible to take multiple images of a patient with a single camera that is moved around the patient to capture multiple images at different angles if the patient remains very still. A single camera can also be coupled to a lens system that can capture images of the patient from suitable angles and positions.

In order to get an accurate surface position, each of the reference points on the body must be visible in two or more photographs or images. The images are analyzed by a computer surface reconstruction program. The program triangulates the reference points through photogrammetry also known as digital image correlation to determine a surface geometry of the body. In addition to the reference points, additional features of the device as marked on the patient are also shown in the images and visible to the CAD program operator. The features can include edges of the brace or device, holes, pads, windows, hinges, different materials and other features. The system operator or the CAD software can identify the features and add the features at the marked locations on the brace or device. Frequently when a brace or cast is needed, the patient is suffering from some internal injuries and additional information such as MRIs or X-rays are available. In an embodiment, the photogrammetry can be combined with the MRI or X-ray data to identify the locations or regions that need to be accessible or the locations of bones that are sensitive to abrasion. By integrating the MRI and/or X-ray data, the device can be made more accurately. The use of data from the other modalities is especially useful in identifying the axis of rotation of the joint accurately in all planes to render a more accurate range of motion brace.

In addition to the features marked in the photographs, the designer can use the system to add additional features including ventilation holes, flexible pads, cushioning recesses, flexibility slots, etc. The designer can also specify the brace or device materials and thicknesses. In some applications, the designer can specify a plurality of materials used in the brace. A strong and hard material can be specified in areas that require structural strength while a flexible material can be specified over areas that require flexibility and/or cushioning. The brace design is a data file that includes the physical dimensions of the device that has an interior surface that matches the body contours determined by the photogrammetry process and additional features.

In some situations, the brace or device may not match the scanned surface data. For example, a patient may have scoliosis and may need a corrective back brace. The brace may be used to correct the curvature of the back to reduce the deformity. Photographs of the back can be taken to obtain the surface data. However, rather than designing a back brace that uses the detected spine location, the back data can be modified to help straighten the back. In this embodiment, the software can be used to design a back brace that is straighter than the measured back. The system can obtain measurements for the overall length and curvature of the spine and the operator can adjust the brace design to be straighter. In one embodiment for the sizing of a back brace, the physician can mark the spinous processes of the scoliotic patient. The curvature of the back and location of the spinous processes is then captured by photogrammetry. The provider can then correct the brace morphometry to adjust the curve reference points to provide the corrective molded brace. The actual difference(s) between the brace and the normal back position can be specified by the patient's doctor.

In addition to the scanned surface data and device features, the CAD system can also design flexibility and ventilation holes into the device. The designer can select one or more materials for the device and the CAD system can know the mechanical properties of these materials. The operator can then input the flexibility characteristics which can include flexibility in one rotational or bending direction and more rigidity in a second rotational or bending direction. The designed flexibility can also include multiple flexibility characteristics for different regions of the device. For example, a first region of the device can have a first bending flexibility and a first axial rotation flexibility and a second region of the device can have a second bending flexibility and a second axial rotation flexibility. The device can also be designed to have a directional flexibility meaning that the device can bend, rotate or otherwise deform in a specific direction. For example, in an X, Y and Z coordinate system, the directional flexibility may allow bending or rotation about the X axis but be stiffer in other directions to resist bending or rotation about the Y axis and/or Z axis. The CAD system can be used to design holes into a device that provide a calculated flexibility to the device. The factors that will influence the flexibility include material characteristics, material thickness, hole size, shape and orientation. In addition to providing flexibility, the holes will also provide ventilation to the patient which will also increase comfort. In an embodiment, the flexibility can be quantified by the bending force required to move the device a given deflection distance or bending angle or the rotational torque required to rotate a portion of the device a given angular rotation.

Additional features of the device include a modular construction. This is useful when used for a broken bone in a limb such as a forearm. The inventive modular cast can be designed for a patient that can have several modular sections that can be removed sequentially as the patient heals. The doctor can mark the patient to indicate the different modular sections and the modular section markings will be detected by the photogrammetry and the brace can be designed with the marked modular sections. The brace can then be fabricated and the different modules can be secured to each other with a joint mechanism or any other type of removable fastener so that the different sections can be individually removed as the patient heals. If a patient breaks an arm, the entire arm may initially be immobilized in a modular brace that extends from the fingers to the shoulder. After a first period of about 2-3 weeks the upper arm module can be removed. After a second period of about 2-3 weeks, the elbow and/or thumb modules can be removed. The lower arm (short arm cast) module can be worn to support the arm until the bones heal. Since the modules are simply removed, the cast is not destroyed and new casts are not required. This is a substantial benefit to the patient and doctor because much less time and resources are required. A similar modular brace can be used for an injured hand, leg or foot. As the patient heals, portions of the brace can be removed to allow for comfort, movement and ventilation.

A modular design or a design using multiple material designs can also be used for braces worn by growing children. Back braces can fit a child patient for several months or much longer. However in order to be comfortable, the brace must be able to adapt to the growth of the child. The bones around the hips tend to grow as the child develops and without a flexible or a modular design, the child will periodically require an entirely new brace. This growth will require refitting the patient whenever the brace is replaced. In order to prevent or minimize the replacement, the brace can be designed with flexible sections and/or modular components. For example, a back brace can be designed with a flexible or elastic modular portion around the hips that allow for growth. When the hip module cannot accommodate the patient any longer, this modular hip section can be replaced with another hip module that properly fits the patient. The modular hip section can then be attached to the rest of the brace and used until the child's growth requires another replacement module.

Modularity is also important in the final fitting of the patient. Specific regions of back braces frequently can be difficult to fit to the patient. The printing or constructing a brace is costly and time consuming. If the brace does not fit well in a specific region, the use of modular panels allows the malfitting section of the brace to be specifically replaced without needing to replace the entire construct.

In yet another embodiment, a brace or cast can be designed having a plurality of accessible regions. Each region can be attached to a hinge or other releasable fastener that allows the portion of the brace for access to the patient. This can be designed over a specific area of interest, for example a wound area that needs to be cleaned or periodically checked and then protected again. By placing a number of these accessible regions adjacent to each other, the body can be cleaned by opening each region individually while the rest of the body is held within the device. The inventive brace allows improved comfort and hygiene while still protecting the patient during the healing process. For example, medical procedures may require placing pins or other objects in a patient. It may be necessary to avoid contact with and allow inspection of these areas. By using an access region over these areas, the doctor will be able to inspect the area to insure that the patient is healing properly. The accessible region feature can also be particularly useful for infants who will need to be cleaned regularly. The inventive brace can be designed with access to the lower torso regions that allow the child to be cleaned. The region can be opened for cleaning and then closed after cleaning is completed. This design is a significant improvement over casts that must be partially sawed to access the child for cleaning.

After the brace or device is designed, the brace design data is transmitted to a fabrication machine that constructs the brace. In an embodiment, the fabrication is rapid prototyping, rapid manufacturing, layered manufacturing, 3D printing, laser sintering, and electron beam melting (EBM), fused material deposition (FDM), CNC, etc. The fabrication machine produces a three dimensional single or multiple piece structure that can be plastic, metal or a mix of different materials. In order to efficiently produce the described devices, it can be desirable to simultaneously produce as many component parts as possible. Many fabrication machines can produce parts fitting within a specific volume in a predetermined period of time. For example, a brace can fit around the torso of a patient and have a large space in the center. This brace can be made, but it will only make one device. In order to improve the efficiency, the brace can be designed as multiple pieces that are later fused together. Rather than making a single brace with the large open center area, the described fabrication methods can be used to simultaneously produce components for two or more braces that occupy the same specific volume. By laying out the components in an efficient production manner for fabrication by an additive material machine, the cost of fabrication can be significantly reduced. The components can then be assembled and fused together to form the brace. Padding and other components can be added to the brace after the brace shell has been fabricated.

The use of a photographic process has many advantages over other surface scanning technologies. The process for transposing the locations of features from the patient to the brace or device is simplified because the doctor can apply location marks to the patient directly or on a form fitting covering. Thus, the locations of the features are much more likely to be accurately placed on the final product. The equipment costs are also reduced because the digital cameras, computers and electronic memory are inexpensive. The photo equipment is also portable, so it can be easily transported to patient's location. The digital data can then be transmitted electronically to a fabrication machine located at a guild. Alternatively, the digital device data can be recorded onto a disk and transmitted to the fabrication machine.

The inventive custom design process is unique because it provides a virtual fitting of the brace to the patient prior to fabrication of the actual device. No other known system provides the ability to design custom products such as braces in a virtual manner. In particular, the inventive process can detect marking placed on a body and utilize this information to design the product based upon the location of the mark.

While the device has been described as a medical device, such as a brace or cast for humans, in other embodiments, it is possible to use the inventive process for other products used by humans including: custom chairs, seats, saddles, athletic equipment, shoes, padding, helmets, motorcycle and bicycle seats, handlebars and hand grips, etc. The described apparatus and method can also be used for braces and casts for animals and custom saddles for horses and equestrians.

BRIEF DESCRIPTION OF THE DRAWINGS

FIGS. 16-18 illustrate multiple views of a brace;

FIGS. 32-36 illustrate a modular brace;

DETAILED DESCRIPTION

Figure 1:
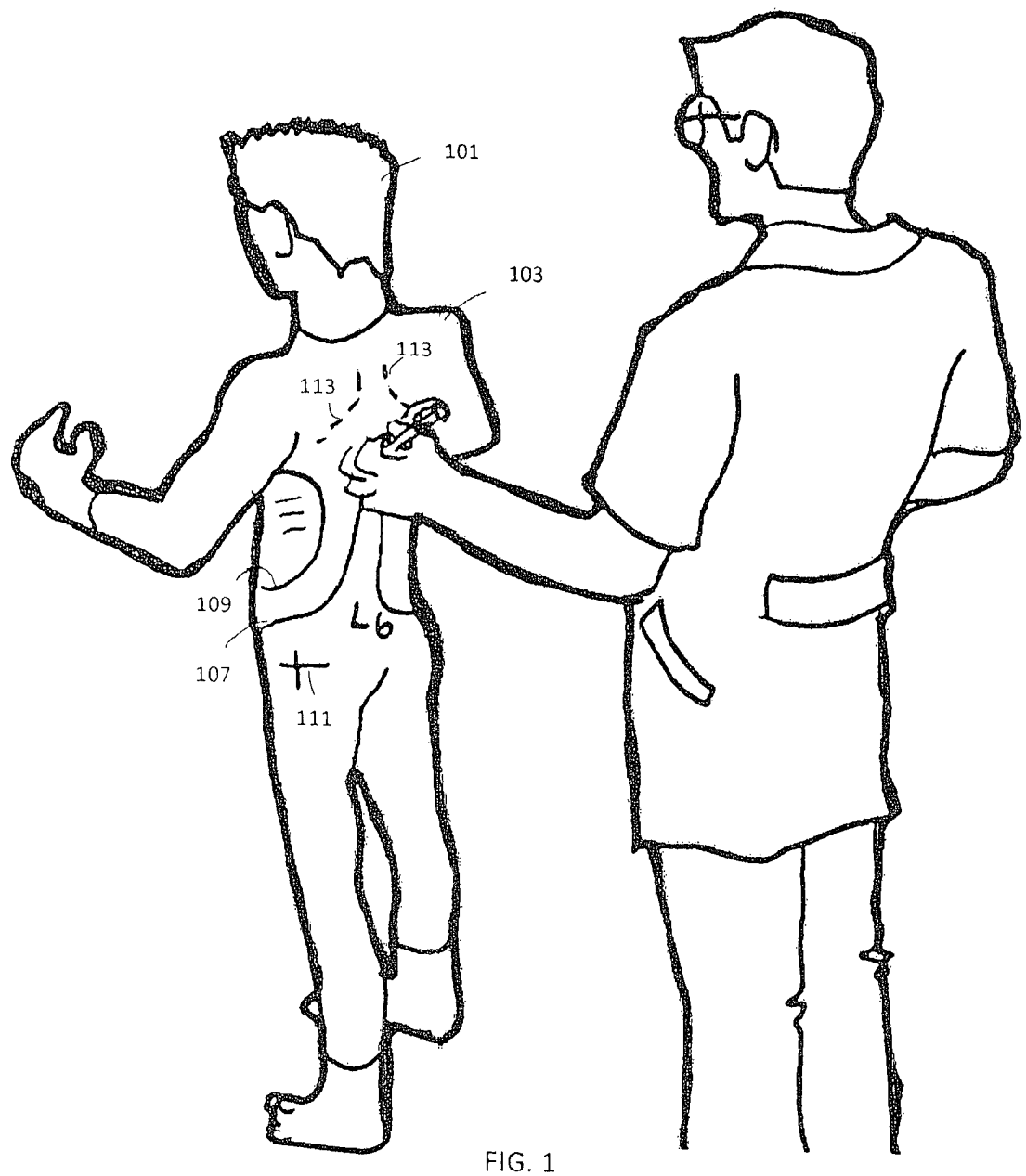
FIG. 1 illustrates a patient being marked by a doctor for back brace fabrication.

The present invention is a custom designed a cast, a brace or another device having a surface that corresponds closely to a body. The cast or brace has an inner surface that corresponds closely to the patient's body and may also have an integrated construction. The inventive cast or brace is directed towards injured backs, legs and arms or other body parts. The cast or brace is preferably designed by an industrial designer using a Computer Aided Design (CAD) computer program. The mechanical data for a patient can be obtained from photographs of the patient's body. This body data is then digitized and input into a CAD program that is referenced to design the cast or brace. An example of a suitable CAD program is Pro/Engineer by Parametric Technology Corporation. Other CAD software includes: SolidWorks by SolidWorks Corporation a subsidiary of Dassault Systèmes, S. A. For simplicity, the inventive custom brace, cast or device will be described as a back brace, however the same processes can be used to form an arm or leg brace or any other body brace, cast or device. The brace can be a hard and strong structure that is designed to surround and support the injured portion of the body or limb.

For example, a leg brace is created for a patient using a CAD system. The leg brace can include an upper leg, knee, lower leg, and foot and have an interior surface that matches the mechanical dimensions and surface contours of the patient's leg. In order to accurately create an interior surface that matches the patient's leg, the surface counters of the user's leg are measured.

The measurement of the outer surface of the leg can be obtained in several different ways. In a preferred embodiment, a photogrammetry or image correlation technique is used to obtain the outer surface measurements which can be a set of 3-dimensional coordinates that define the outer surface of the patient's leg or any other body part.

Photogrammetry in its broadest sense reverses the photographic process by converting flat 2-dimensional images of objects back into the real 3-dimensional object surface. Two or more different photographs are required to reconstruct a 3-dimensional object. In a perfect photogrammetry process, two photographs would provide enough information to perfectly reconstruct the 3-dimensional object. Unfortunately, the photography and measuring process are generally not perfect so the reconstruction of the 3-dimensional object based upon two photos will also have defects. The photogrammetry object measurement process can be improved by taking more photographs and using the extra information to improve the accuracy. The photogrammetry process will produce a set of 3-dimensional coordinates representing a surface of an object from the measurements obtained from the multiple photographs.

Photogrammetry uses the principle of triangulation, whereby intersecting lines in space are used to compute the location of a point in all three, XYZ dimensions. In an embodiment, multiple cameras are used to photograph the leg or body part simultaneously. In order to triangulate a set of points one must also know the camera positions and aiming angles also called the "orientation" for all the pictures in the set. A process called resection does the camera position and aiming angle calculations for each camera. The cameras should also be calibrated so their errors can be defined and removed.

Triangulation is the principle used by photogrammetry to produce 3-dimensional point measurements. By mathematically intersecting converging lines in space, the precise location of the point can be determined. Photogrammetry can simultaneously measure multiple points with virtually no limit on the number of simultaneously triangulated points. By taking pictures from at least two or more different locations and measuring the same target in each picture a "line of sight" is developed from each camera location to the target. Since the camera locations and aiming directions are known, the lines can be mathematically intersected to produce the XYZ coordinates of each targeted point.

Resection is the procedure used to determine the coordinates of the object from photograph data, based upon the camera positions and aiming directions, also known as the orientation of the camera. Typically, all the points that are seen and known in XYZ coordinates in the image are used to determine this orientation. For an accurate resection, you may have at twelve or more well-distributed points in each photograph. If the XYZ coordinates of the points on the object are known, the camera's orientation can be computed. It is important to realize that both the position and aiming direction of the camera are needed for resection. It is not sufficient to know only the camera's position since the camera could be located in the same place but be aimed in any direction. Consequently, the camera's position which is defined by three coordinates, and where it is aimed which is defined by three angular coordinates must be known. Thus, although three values are needed to define the X, Y and Z coordinates of a target point, six values may be required to define a point on a picture, XYZ coordinates for position, and XYZ angles for the aiming direction.

The surface being photographed should also have a minimum number of well-distributed reference points that appear on each photograph and for an accurate surface measurement. The reference points can be visible marks placed on the object that provide a visible contrast that will be clearly shown on the photographs. There should be at least twelve well-distributed reference points on each photograph and at least twenty points for the entire surface of the object. The reference points should be evenly distributed on the object and throughout the photograph. The surface of the object can be more accurately measured with a larger the number of reference points.

While it is possible to mark the patient's skin with ink markers, in a preferred embodiment, the patient is covered with a form fitting material such as an elastic cotton tube, stockinette, leotard, body suit. In other embodiments, the body can be wrapped with a form fitting material. In another embodiment, the body surface can be sprayed or painted with removable materials such as a flexible plastic or rubber material that conforms to the body and can marked and easily removed after images are captured. With reference to FIG. 1, a patient 101 is illustrated wearing a body suit 103 that covers the patient's body, arms and legs.

In an embodiment, a computer program processes the photographic measurements to produce the final XYZ coordinates of all the measured points. In order to do this, the program triangulates the target points and resects the pictures. The program may also calibrate the camera. Typical accuracies of the three dimensional measurements can be very high under ideal operating conditions. For example, the measurements can be accurate to 50-100 microns (0.002" to 0.004"). However, the accuracy of a photogrammetric measurement can vary significantly since accuracy depends on several inter-related factors. Important accuracy factors include: the resolution and quality of the camera, the size of the object being measured, the number of photographs taken, and the geometric layout of the pictures relative to the object and to each other.

Photogrammetric measurements can be dimensionless. To scale a photogrammetric measurement, at least one known distance is required. The known distance can be a distance marked on the object. For example, if the actual coordinates for some targeted points are known, the distances between these points can be determined and the points can be used to scale the measurement. Another possibility is to use a fixture with targets on it and measure the fixture along with the object. Because the distance between the targets on the fixture is known, it can be used to scale the other measurements between reference points on the object. Such fixtures are commonly called scale bars.

In an embodiment, the inventive method is used to make a cast or a brace for an injured limb. A series of photos are taken of the injured limb. If the bone is broken, fracture should be reduced before the photos are taken. The photogrammetric processing methods described above are then used to obtain the surface coordinates of the injured limb. In order to define common surface points on the limb, reference points can be placed on the limb. The reference points can simply be any contrasting color points, patterns, shapes, objects, symbols or other optical indicators which are easily visible. The reference points can be black or colored ink marks, stickers or objects or any other visible point of reference. In the preferred embodiment, the reference points are placed and evenly distributed around the entire limb or portion of the body that the brace is being constructed for.

In addition to the reference points, the patient can also be marked to define an edge of the brace or other features. With reference to FIG. 1, the doctor can mark the body suit 103 with a pen 105 to define the locations of the edge of the brace. The edge marking can be one or more continuous lines 107 that extend around the body or limb. In other embodiments, the edge can be defined by a series of marks that define the edge of the brace and are connected during the brace design. Additional lines 109 can also be marked on the patient to create openings in the brace. For example, the patient may have injured areas from an operation that has been closed with stitches and should not be in contact with the rigid brace. By providing an opening in the brace, the patient's stitches will not be pressed against the brace structure. In FIG. 1, the doctor has drawn a circle around this portion of the patient's body so that the brace can be designed with a cut out for this area. The doctor can also make notes on the body suit 103. The doctor has written "L6" to indicate the location of the L6 disk. The doctor has also marked a cross 111 at the greater trochanter of the femur and dashed lines at the shoulder blades 113. These anatomical locations are important in the design of the brace and are therefore marked on the body suit 103. Because photogrammetry uses photographs, the digital pictures will record all of the lines or other markings.

Figure 2:
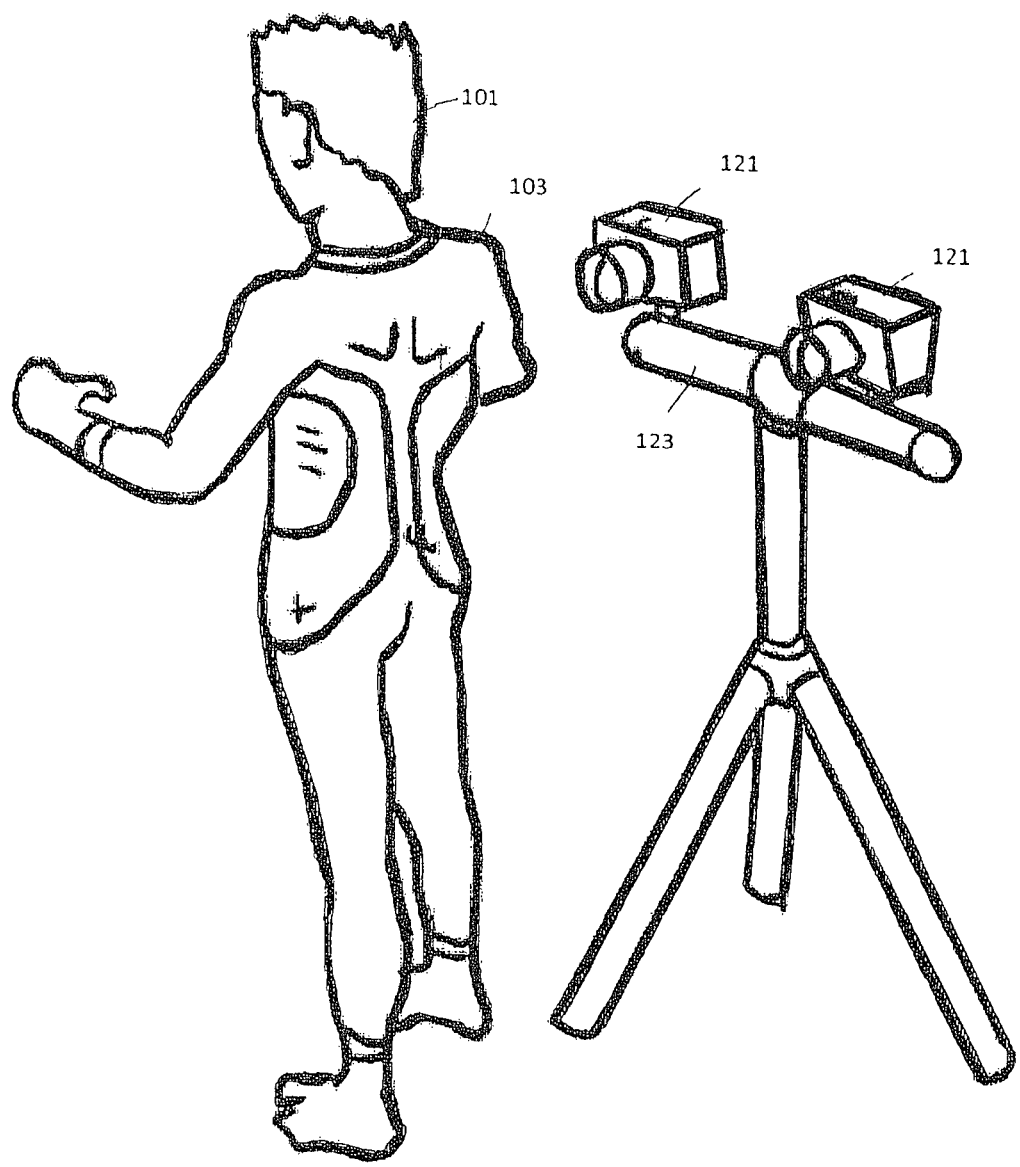
FIG. 2 illustrates the marked patient being photographed.

With reference to FIG. 2, photographs of the patient are taken with a plurality of digital cameras 121. In this example, the cameras 121 are mounted on a bracket 123 and horizontally separated by a known distance. The cameras 121 have the same horizontal position and the lens can be in the same plane and angled inward towards each other. The angle of the lenses can be between about 5 to 45 degrees. The distances between the patient 101 and the cameras 121 are also known. The two cameras 121 can be actuated simultaneously so that the two or more photographs will represent the patient 101 in the same position. In order to get the body contour information, pictures are taken of the patient 101 wearing the marked body suit 103 from various angles around the entire circumference so that all surfaces of the body that will be covered by the brace. Each photograph should include at least twelve of the reference points. By processing the photographs and triangulating the reference points and other lines and markings in the photographs, the coordinates representing the body surface can be obtained.

Figure 3:
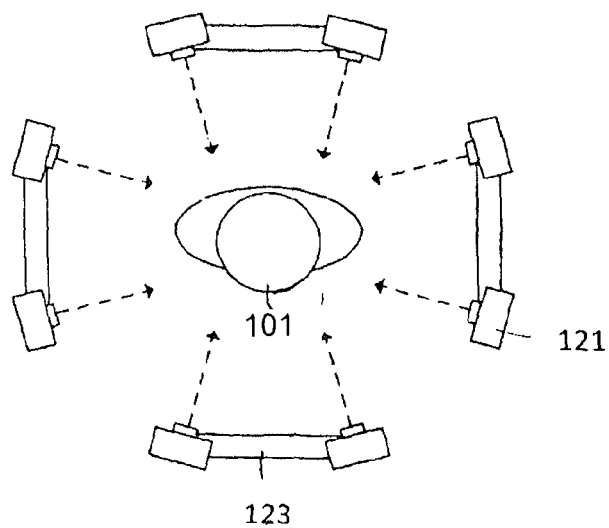
FIG. 3 illustrates a top view of a patient being photographed by a plurality of cameras.

With reference to FIG. 3, a top view of a camera 121 system used to photograph the patient 101 and body suit 103 is illustrated. In an embodiment, an apparatus that includes a plurality of cameras 121 that are mounted on brackets 123 and positioned around an open space can be used to photography the patient 101. The cameras 121 are pointed in towards the patient 101 and arranged in groups of two cameras 121. The cameras 121 can be mounted on brackets 123 that hold the cameras so they are generally pointing in the same direction but angled slightly towards each other. The cameras 121 can be positioned with the lenses horizontally aligned, but rotated slightly about a vertical axis, so the camera 121 lenses are not parallel. This angle allows the cameras 121 to analyze the difference in the surfaces so that a 3-dimensional representation is generated, much as it is with human stereoscopic vision.

In this example, four groups of cameras 121 are mounted around the patient 101 with each group having two cameras 121. Thus, eight photos each from different angles are taken of the patient 101. The pictures taken by the cameras 121 together cover the entirety of the torso. The camera 121 positions can be moved depending upon the area of interest. In the illustration, the cameras 121 may be configured to collect data for a back brace. However, if a leg brace is being made, the cameras 121 can be lowered to a position around the leg.

An actuator can be coupled to each of the cameras 121 and used to cause all of the cameras to photograph the limb simultaneously. Alternatively, the camera 121 pairs can be synchronized to all take pictures simultaneously to capture the images of the object at the same time. Since the shutter speed is typically just a fraction of a second, there is no need to keep the patient 101 absolutely still for an extended period of time. In other embodiments, a single camera can be used to capture multiple images of the patient. In this embodiment, the camera can capture multiple images simultaneously or in a short period of time. The camera can have multiple lenses each capturing a different image. Alternatively, the patient can move relative to the camera. By rotating the patient or rotating the camera about the patient and taking multiple photographs, a single camera can capture multiple images that can be used to obtain the surface topography and other marker data.

As discussed above, the photographs are processed and used to generate three dimensional data that accurately describes the outer surface of the patient 101. The three dimensional data is then used to design and fabricate the brace or cast. Because the surface data is very accurate, the brace or cast will have a custom fit that accounts for all detected surface contours. In addition to the custom fit interior surface, the edges or brace features are also clearly defined by the edge or feature markings and can be used to assist in the design of the brace or cast.

In some cases, the physical condition of the patient is such that the photogrammetry images will not result in an accurate brace. For example, if a patient has injured a limb, the area of injury can be swollen. Thus, any photographs of the limb will result in a scan data that is much larger than the unswollen limb. In an embodiment if the patient has an intact limb that is similar to the damaged limb, the intact limb can be photographed and the surface data obtained from the intact limb can be reversed in a mirror manner to create the required data for a brace for the damaged limb. The brace can be designed and fabricated so that when the swelling goes down, the brace will be ready for the patient.

Photogrammetry also has various benefits over other types of surface scanning methods including optical and laser scanning because it can also be used to detect markings placed on the patient by a doctor which can be used to indicate special portions of a body or the brace. For example, a doctor can draw on the patient to demark any number of notes that they will reference later in the custom device process. These marking may indicate: boundaries of the custom prosthetic/orthotic, areas of bony protuberances, folds of adipose tissue, specific reference vertebrae, sensitive areas on the body (rashes, birthmarks, moles, etc) to be avoided, areas that will require enhanced ventilation, clearance areas around joints to allow unencumbered motion, setup notes, reference boundaries for 'shims' which will later add additional pressure within the brace and various other information. The body markings can be colored points, lines or symbols, textured markers or other codes that are used to identify the different types of reference points on the patient. For example, a patient may be marked with a first color to indicate a desired boundary of the brace or cast. The patient can also be marked with a second color or textured marker to indicate a bony protuberance or sensitive areas. Since the bony protuberances, or underlying bony anatomy are areas prone to skin breakdown, the brace can have special features over these areas to avoid abrasion or damage to these areas. For example, during the design process, the operator can reduce the brace over the areas of the patient's body marked as bony anatomy. An example is the placement of the brace over the regions of the scapula. The scapula and its borders can be palpated manually but are difficult to determine based on surface morphology. The brace must accommodate for the scapula to function properly. In the techniques the location of the edges or body of the scapula is marked on the patient and the body of the brace will accommodate the bony edges with custom padding or relief in the brace contour.

The brace will require pads to be comfortable to the patient. The locations of the pads can be marked on the patient as described above. For example, a pad location and shape can be indicated with a coded marking in the shape of the pad. The CAD system will detect the pad marking and be able to fabricate a pad that matches the designated shape. During the fabrication process, the pads can be fabricated from a soft elastic material in a range of thicknesses and firmnesses. For example, the CAD data can be used to cut the pads from a sheet stock of pad material. The CAD system can also design the brace to accommodate the pads. For example, the brace can be designed and fabricated with recesses formed at the coded and marked areas or other attachment mechanisms. Since the patient surface data is used to form both the brace and the pads, they will fit together very accurately. If there are ventilation holes designed into the brace over a pad location, the pad can also be designed with ventilation holes that is aligned with the ventilation hole in the brace.

When the brace is fitted to the patient, the doctor will have a plurality of pads and will be able to select the best pad thickness for the patient. Because the brace can be made of a strong and durable material, the pads can be worn with use of the brace and may need to be replaced periodically. The doctor can have additional pads fabricated from the brace data. Additional pads can also be made using additive manufacturing processes such that the pads have an outer surface that is conforming to the brace and an inner surface that is conforming to the patient's anatomy in areas with complex surface geometry such as bony prominences such as the iliac crest.

In other embodiments, the coded marking can be a pattern, symbol, a textured pad, bar code, 3-D objects or other indicators. Because these cameras use the photographic image for their data input, the coded markings or topography on the patient can be identified by the brace/cast design software. The inventive process may be able to distinguish different color codings as well as different pad textures. The textures can include grooves, etched patterns, convex or concave surfaces, etc. Each texture may represent a different feature of the brace at the marker location. The detection system software may automatically detect and identify the coded color or texture. The software can then automatically design the requested feature of the brace associated with the coded color or texture was positioned on the patient. The additional markings will be transferred to the digital representation of the patient and be used to help design the brace or cast.

Figure 4:
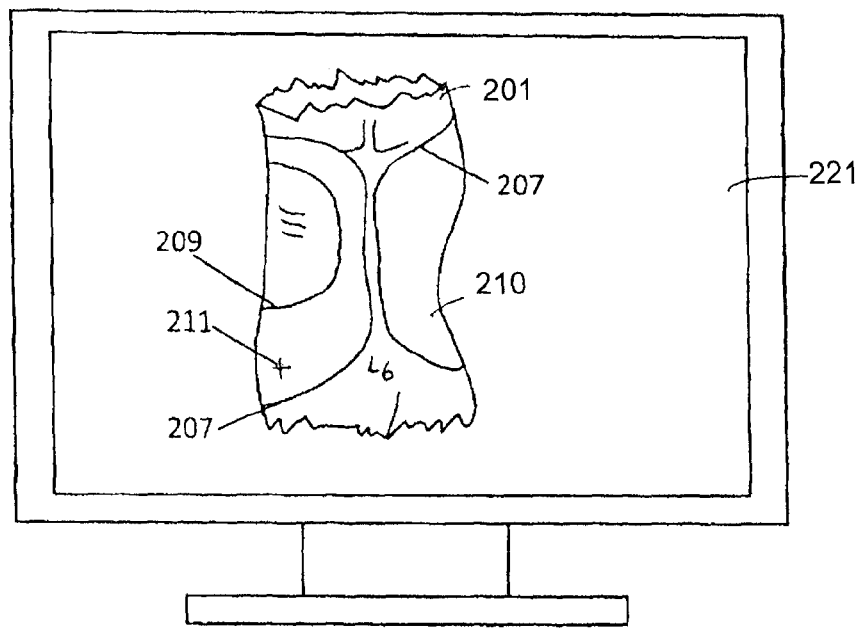
FIG. 4 illustrates a computer displaying a digital representation of a portion of the patient.

The process by which the scanned body data is used to design a brace is illustrated in FIGS. 4-8. FIG. 4 illustrates a scanned image of a human torso 201 on a CAD screen 221. The contours of the torso 201 are accurately measured and the additional markings that were placed on the patient are also illustrated on the scan data. In this example, the doctor has drawn a cross 211 of the patient's greater trochanter of the femur so the brace is designed with extra space in this area for movement of the leg. Line 207 indicate the desired boundaries of the brace and line 209 indicates a hole in a side of the brace. The notation "L6" is also visible from the photogrammetry scan data.

Figure 5:
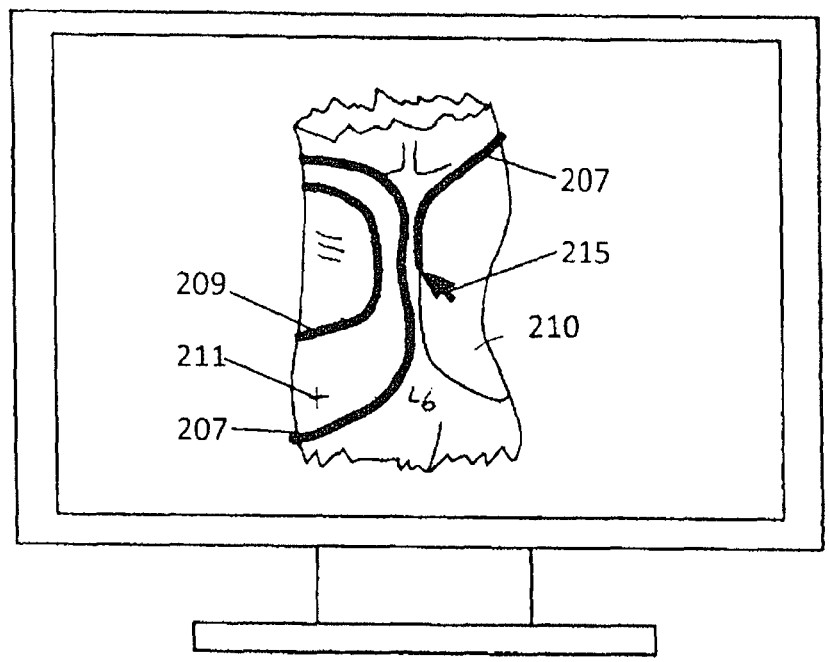
FIG. 5 illustrates a computer displaying the design process for a back brace.

With reference to FIG. 5, the line 207 representing the edge of the brace is being highlighted. The line 209 representing a hole to be formed in the brace has been highlighted by the brace designer. In this embodiment, a mouse controlled cursor 215 is used to highlight the lines. In other embodiments, the designer can select click on the line to highlight the entire line. In this example, the darker line represents the portions of the line to be removed from the brace. However, any other visual markings can be used to identify the portions of the line to be removed.

In some situations, the brace or device may not perfectly match the scanned surface data of the patient. For example, the designer can also account for the marked cross 211 representing the location of the greater trochanter of the femur bone. The marking will be indicated on the images captured during photogrammetry and the cross may be a designated symbol indicating the location of the greater trochanter. The software can then adjust the design of the brace over the greater trochanter by expanding this portion of the brace.

In another example, a patient may have scoliosis and may need a corrective back brace that changes the normal posture of the patient. The brace may be used to correct the curvature of the back to reduce the curvature deformity. Photographs of the back can be taken to obtain the surface data as described above. However, the actual spine position may not be detected unless the surface shows the back bones as surface features. In order to clearly indicate the spinous processes of the back, the doctor may need to mark the location of each. The marking can be coded to identify the specific bones or indicate a bone that is damaged. The markings can surround the bones, be a cross mark, or any other mark that clearly identifies the locations of the bones. When the photogrammetry images are processed, the locations of the spinous processes will be clearly indicated. The back surface and spinous processes locations can then be used to design the back brace.

Rather than designing a back brace that uses the detected spine position, the back data can be modified to create a brace that straightens the patient's back. The designer can obtain measurements for the overall length and curvature of the spine and the desired curvature alteration of the brace. The difference between the brace and the normal back position can be specified by the patient's doctor. The designer can then adjust the recorded back curvature to design a back brace that is straighter while maintaining the desired interior volume defined by the brace. In an embodiment, the design program can include a system for adjusting the brace design which allows for the adjustments of one part of the brace to be carried over to the other portions of the brace. For example, if the back data shows the photographed spinal curvature, the designer can manipulate the apex to reduce the curvature. Rather than adjusting only the apex portion, the program will make similar adjustments to the surrounding portions of the brace so that the corrective brace will properly fit the patient. For example, the brace can be divided into many different thin horizontal sections that may each correspond to a different spinous process. When one section is moved, the other sections will move to a lesser degree so that the scoliotic curvature is reduced. An algorithm may be used to scale the movement of the other sections of the brace on the CAD design. By automatically adjusting the different sections of the brace when one section is moved, the brace design is simplified and accurate.

In other embodiments, the designed brace or cast can vary from the photogrammetry measurements taken of the patient. For example, the patient may be swollen due to trauma or inflammation. The brace design system can account for the swelling and allow the designer to create a smaller brace that will fit the patient after the swelling is reduced. In an embodiment, the system can use photographs of an intact limb and use the mirror image surface data as a guide for the brace for the swollen limb. The intact limb may not be a perfect match of the damaged limb, but in many cases it is sufficiently accurate to form a suitable brace or cast.

Figure 6:
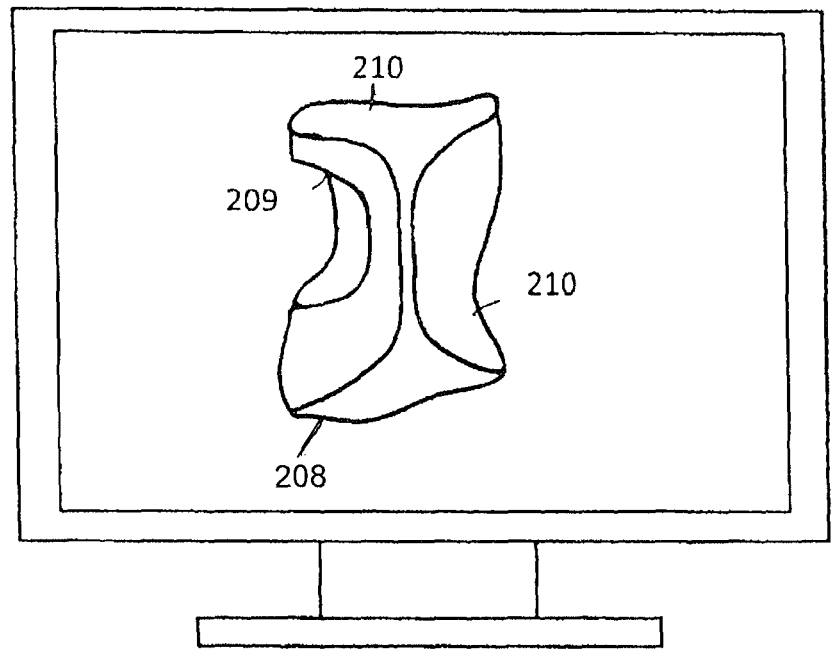
FIG. 6 illustrates a basic back brace designed from the digital representation.

In FIG. 6, the torso is illustrated with the area inside the hole line 209 and torso areas outside the edges 208 removed. Although not shown, designer operating the CAD software can rotate the illustrated torso to show any view of the brace 210. A material thickness can be added to the interior torso surface to create the basic brace design. Because the markings are accurately detected by the photogrammetry system, all of the marked edge and hole positions are transferred to the digital representation and the required brace boundaries and features are accurately identified without having the re-examine or re-measure the patient. The process completes the basic design of the brace 210.

Figure 7:
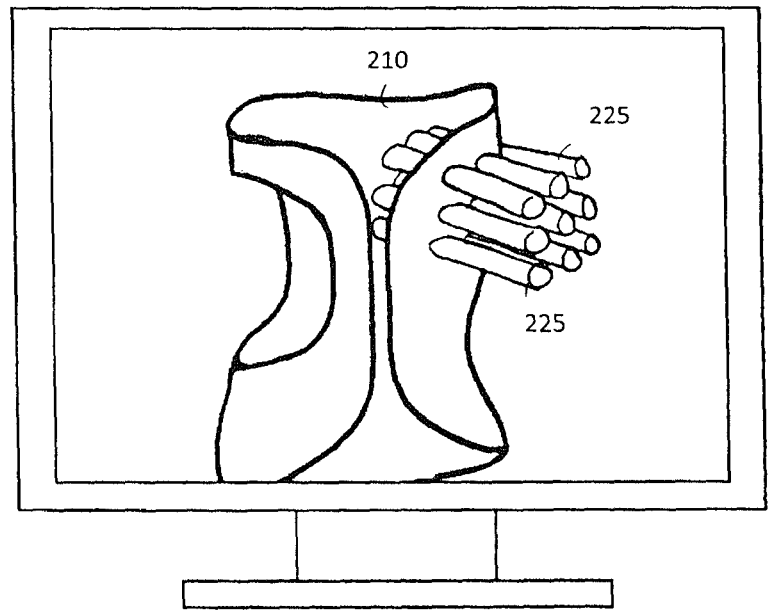
FIG. 7 illustrates a process for designing holes into the back brace.
Figure 8:
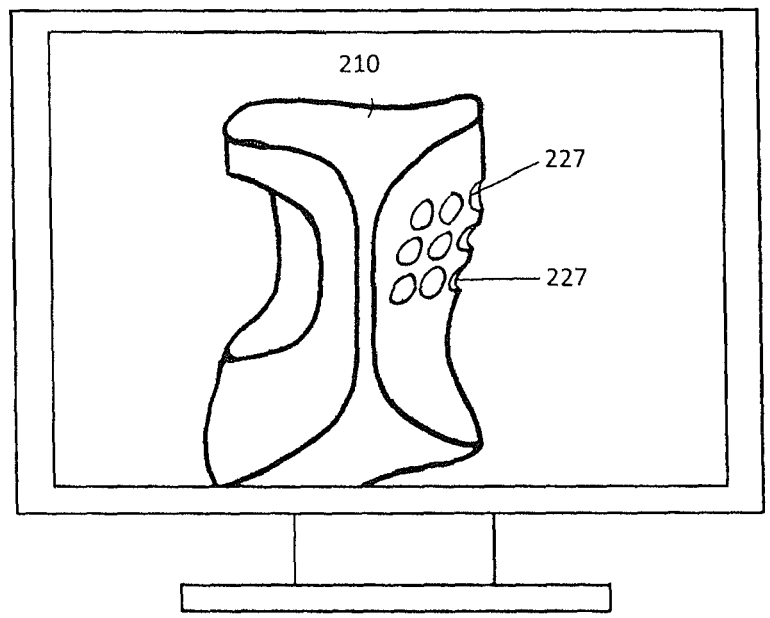
FIG. 8 illustrates the back brace designed with the holes for ventilation and/or flexibility.

In addition to patient features marked on the patient, it is also possible to add additional features to the brace. For example, a plurality of holes can be made in the brace 210 to provide ventilation and flexible portions of the brace. With reference to FIG. 7, the brace 210 is illustrated with a set of cylinders 225 running through a portion of the brace 210. In this example, the cylinders 225 are circular in cross section and define a plurality of circular holes. With reference to FIG. 8, the designer can then remove the material that intersects the cylinders 225 from the brace 210 to produce a brace with a plurality of holes 227.

The structural materials used to fabricate the brace are strong in compression and tension. By forming holes in the brace, ventilation as well as selective flexibility can be added to the brace. By designing openings into the structural material, the structural material can bend rather than be compressed or stretched which allows the brace to have bending movement. The brace designer can design the brace to control the flexibility depending upon the patient's specific needs. The brace can be designed to control the direction(s) of flexibility, the range of movement, the elasticity of the movement, etc. The ability to create details and customized holes and vary these holes regionally in the brace allows for control of motion in bending and torsion independently in different planes, and independently at each level. Articulations built into the brace allow also for controlled motion independently at each level.

Figure 9:
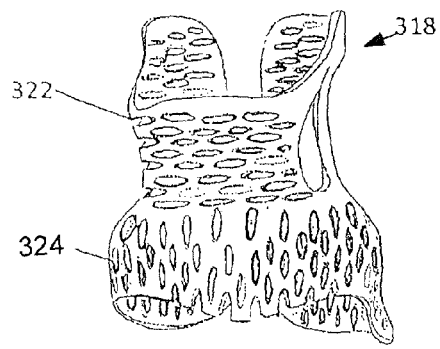
FIG. 9 illustrates a back brace with flexible ventilation holes.

With reference to FIG. 9, a back brace 318 is illustrated having a pattern of elongated holes 322, 324. The holes 322, 324 can add ventilation as well as flexibility to the back brace 318. The designed flexibility can also include multiple flexibility characteristics for the upper and lower regions of the back brace 318. For example, the upper region of the back brace 318 can have a first bending flexibility and a first axial rotation flexibility and the lower region of the back brace 318 can have a second bending flexibility and a second axial rotation flexibility. The holes 322, 324 tend to add flexibility across the width of the holes 322, 324. Thus, in this example, the upper portion of the brace 318 with horizontally oriented holes 322 will tend to allow for vertical flexibility. In contrast, the vertically oriented holes 324 around the lower portion of the brace 318 will allow for more radial flexibility around the brace 318. The lower brace 318 may be positioned over the hips of the patient. As the patient moves and grows, this area may require expansion flexibility.

Figure 10:
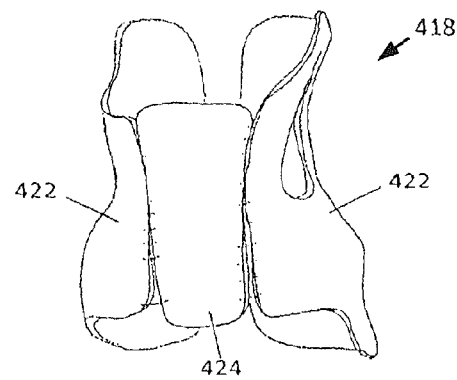
FIG. 10 illustrates a back brace with a flexible panel.

With reference to FIG. 10, a back brace 418 is illustrated made of three parts. Rather than making the brace as a single piece structure, it may be more efficient to produce the brace in three separate parts that are later assembled. It is also possible to make one of the panels out of a different material. For example, the center panel 424 may be a more flexible material than the sides. While the side panels 422 of the back brace 428 may need to be made of a fairly rigid material, the center panel 424 may not require the same strength and may be made of a more flexible material. The center panel 424 can then be secured to the rest of the brace 418 with suitable fasteners.

Figure 11:
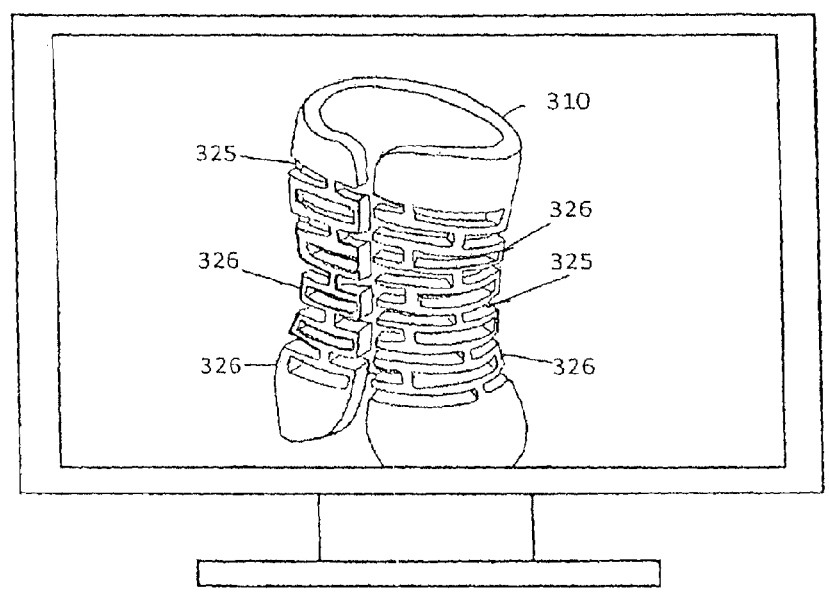
FIG. 11 illustrates a back brace design having horizontally aligned elongated slots for flexibility.

For example with reference to FIG. 11, a back brace 310 is illustrated having a plurality of elongated horizontal slots 325. The slots 325 allow the brace to be vertically flexible but rigid in axial rotation. When a bending motion is applied to the brace 310, the vertical elements will tend to compress the centers of the slots 325. However, when a rotational torque is applied to the brace about the center axis, the brace 310 will be more rigid. In the illustrated back brace 310, the holes on the front and back of the brace are elongated slots 325 that are arranged in offset rows and columns. The slots 325 in each horizontal row are offset relative to the adjacent vertical rows of slots 325. The material between the slots 325 form elongated strips that are mostly horizontally oriented. There are short vertical strips 326 that intersect the center portions of each slot 325. As discussed, the material is strong in compression and tension. Therefore, this design configuration resists torsion or axial rotation of the patient's back. However, because the horizontal strips of material are not aligned vertically, the brace 310 can bend forward and back which allows the patient's back to bend. When the patient bends forward, the front of the brace is compressed and the material bends so the slots 325 at the front of the brace become shorter in height and smaller. Conversely, the back of the brace can be stretched longer and the material can bend so the slots 325 at the back of the brace become higher. In this example, because the slots 325 are wide and short, they are stiffer against horizontal forces while more flexible with vertical forces. In contrast, a slot that is tall and narrow will be stiffer against vertical forces while more flexible with horizontal forces. Thus, the flexibility of the brace 310 can be controlled by varying the size and arrangements of the slot 325 openings.

Figure 12:
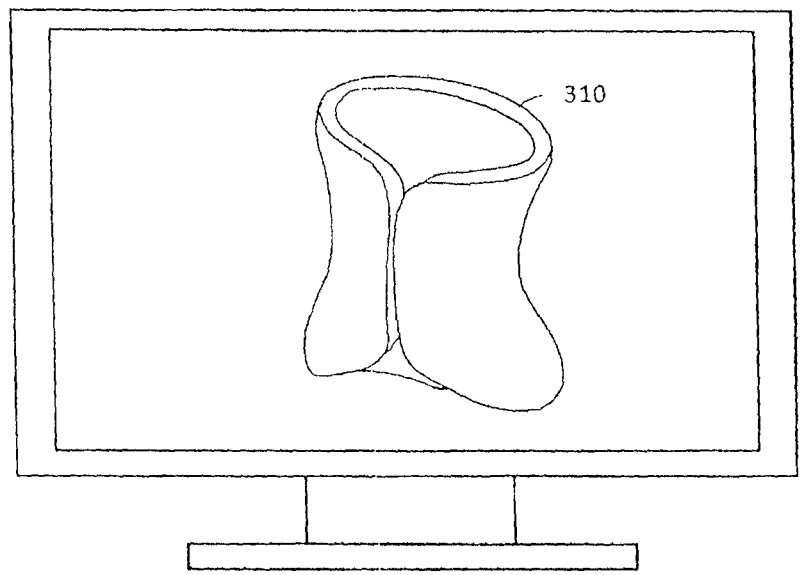
FIG. 12 illustrate the back brace design prior to adding the slots
Figure 13:
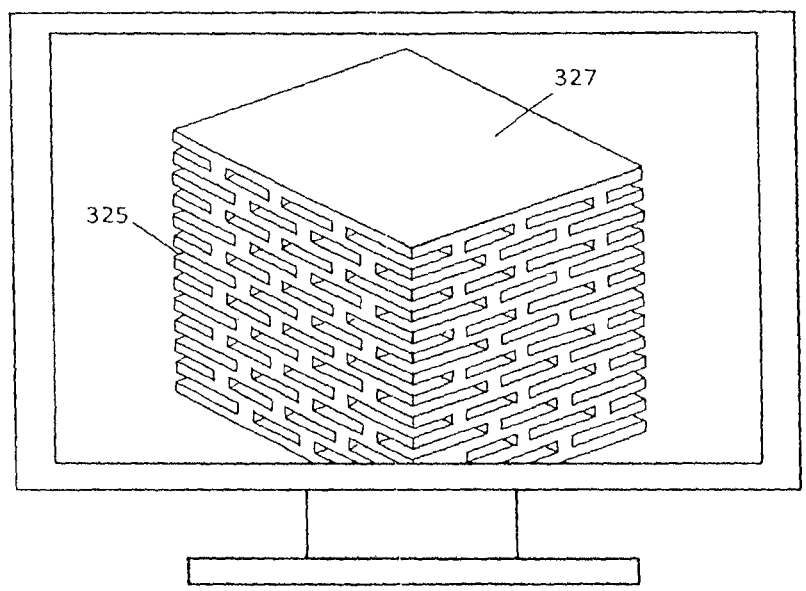
FIG. 13 illustrates a virtual block of material having elongated slots.

With reference to FIG. 12, prior to adding the slots, the back brace 310 design is a solid form that is rigid and does not provide any ventilation to the user as displayed on the CAD software display. Slots 325 or other ventilation holes can be formed by manually adding the slots to the brace design as described above with reference to FIG. 7. Alternatively, a brace 310 with slots can also be added by combining the back brace in a more automated and time efficient manner. With reference to FIG. 13, a block of material 327 is illustrated with preformed slots 325. The designer can input the dimensions of the brace 310 and define the center area of the brace 310 that requires the slots 325.

Figure 14:
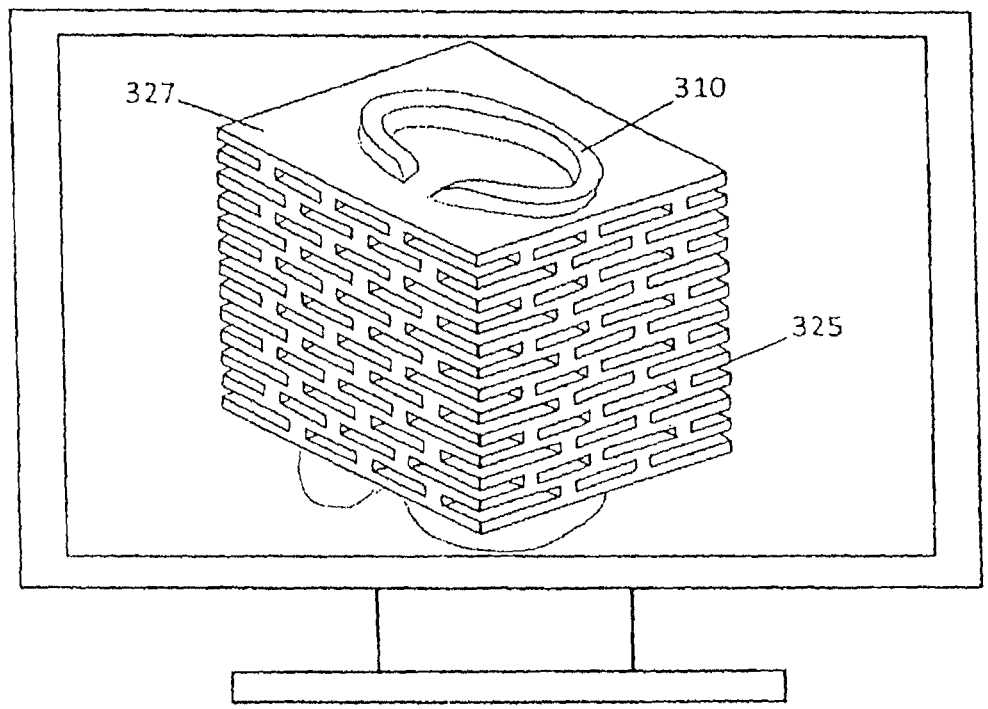
FIG. 14 illustrates the virtual block of material with slots combined with the back brace design.

With reference to FIG. 14, brace 310 and the block of material 327 are virtually combined by the CAD program and displayed on the computer screen. The upper and lower portions of the brace 310 are illustrated without the slots while the center portion of the brace that requires the slots intersects the block 327. The designer can then remove the portions of the block 327 that is outside the brace 310 edges. The resulting brace 310 is designed with a center portion having slots 325 as illustrated in FIG. 11.

In an embodiment, the desired flexibility can be designed into the brace by varying the hole size, shape, orientation, material thickness and fabricating the brace from two more different materials that each have different mechanical properties. These calculations can be integrated into the CAD software so that by inputting the flexibility requirements, the software can compute the details of the brace design that complies with the structural requirements. By modifying the mechanical properties of the brace throughout its shape, it may be inclined to bend, rotate, compress, expand or remain rigid along certain rotational directions as desired. The brace can also be designed to have a directional flexibility meaning that the device can bend, rotate or otherwise deform in one or more specific directions but resist movement in the same way in different directions. For example, in an X, Y and Z coordinate system, the directional flexibility may allow bending or rotation of the brace about the X axis but the brace may resist bending or rotation about the Y axis. The brace can have different directional flexibilities in different regions. In an embodiment, the designed flexibility can be quantified by the bending force required to move the device a given deflection distance or bending angle or the rotational torque required to rotate a portion of the device a given angular rotation. The designed flexibility of the device can also be restricted so that the range of motion is limited to a certain range of movement.

Figure 38:
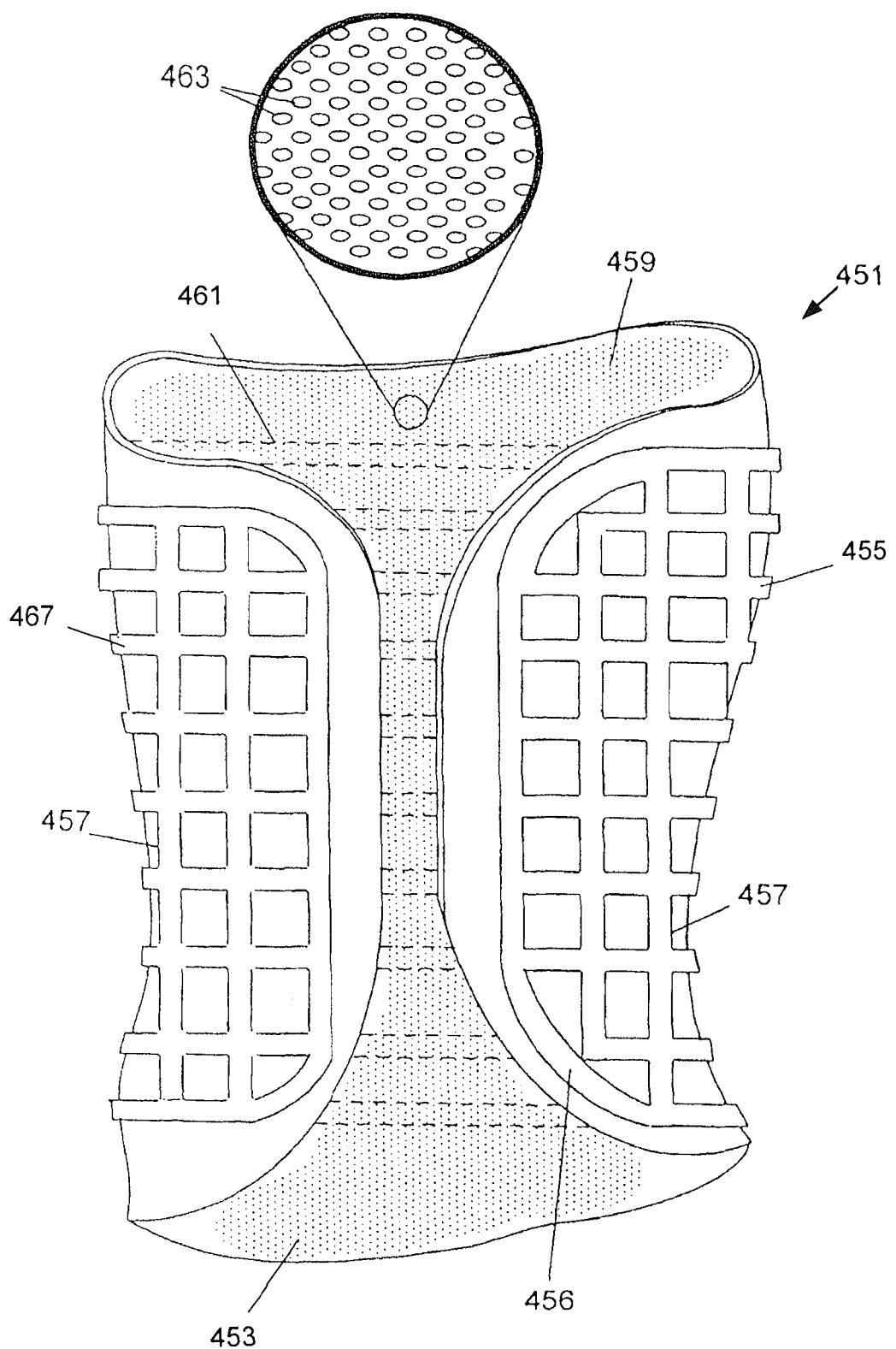
FIG. 38 illustrates brace having an exoskeleton.

With reference to FIG. 38, in an embodiment, the brace 451 comprises a conformal surface 453, a structural component shown as horizontal beams 455 and vertical beams 457, and a 'border' 456 that surrounds the brace 451 and increases structural properties where desired. The back side of the brace 451 is illustrated and the horizontal beams 455 on the front of the brace 451, may compress forward, since there exists no vertical beams 457 to restrict the compression. This would allow forward flexion. Lateral flexion, however, is restricted by the vertical beams 457 on the sides of the brace. Rearward flexion would be restricted by the vertical beams 457 that extend upward along the back of the brace 451.

A thinner layer 459 that is highly perforated can be placed between the structural components. This would offer no structural impact, but is intended to contain the tissue of the patient and prevent the skin from moving into the slots 461 and being pinched during compression of the slots. The ventilation holes 463 can be small (below ⅜"), thereby reducing the chance of 'window edema' problems. This layer 459 behaves as a 'netting' of sorts to contain the body, while not impacting the structural requirements. The holes 463 may be designed in such a way that the surface expands or compresses easily. This may involve holes 463 that are elongated along the horizontal axis, and a grid pattern that is offset (like a checkerboard, rotated 45 degrees) so that no vertical beams are created in the grid, thereby diminishing the structural properties of the surface.

Unlike previous brace technologies, this invention describes a method in which the mechanical properties including bending and rotational properties are specified by the health care professional. The pattern of ventilation is also specified. Then the computer creates the brace to meet the mechanical and ventilation specifications while also matching the conforming shape of the body surface and meeting the overall geometric constraints of the brace. The shape of brace, mechanical properties are chosen, perforation type or design are chosen by health care professional. The brace is then created in which the thickness and width of the structural elements are varied to meet the mechanical and design considerations of the brace. The brace is then produced by additive manufacturing or any other fabrication method.

In many brace applications, the inner surface of the brace must apply pressure without causing skin breakdown. Pressure points must be avoided. The highly conforming brace will minimize contact stresses and will thus minimize the breakdown of skin. However, softer materials may be required over contact points. In addition to minimizing window edema with small perforation internally, with additive manufacturing technology, the inner surface may be constructed of laminated structures produced in continuity with the external exoskeleton 467 to allow the internal layer 459 or layers to be more conforming. Thin deflectable conforming layers may be printed on the inner walls. In other embodiments, completely different materials can be added to the brace. In some other embodiments the brace design and fabrication can include printed mesh or printing a foam like porous material on the inner walls that allow compression and ventilation. The inner layer or layer will be produced by additive manufacturing with all layers produced in continuity.

Figure 39:
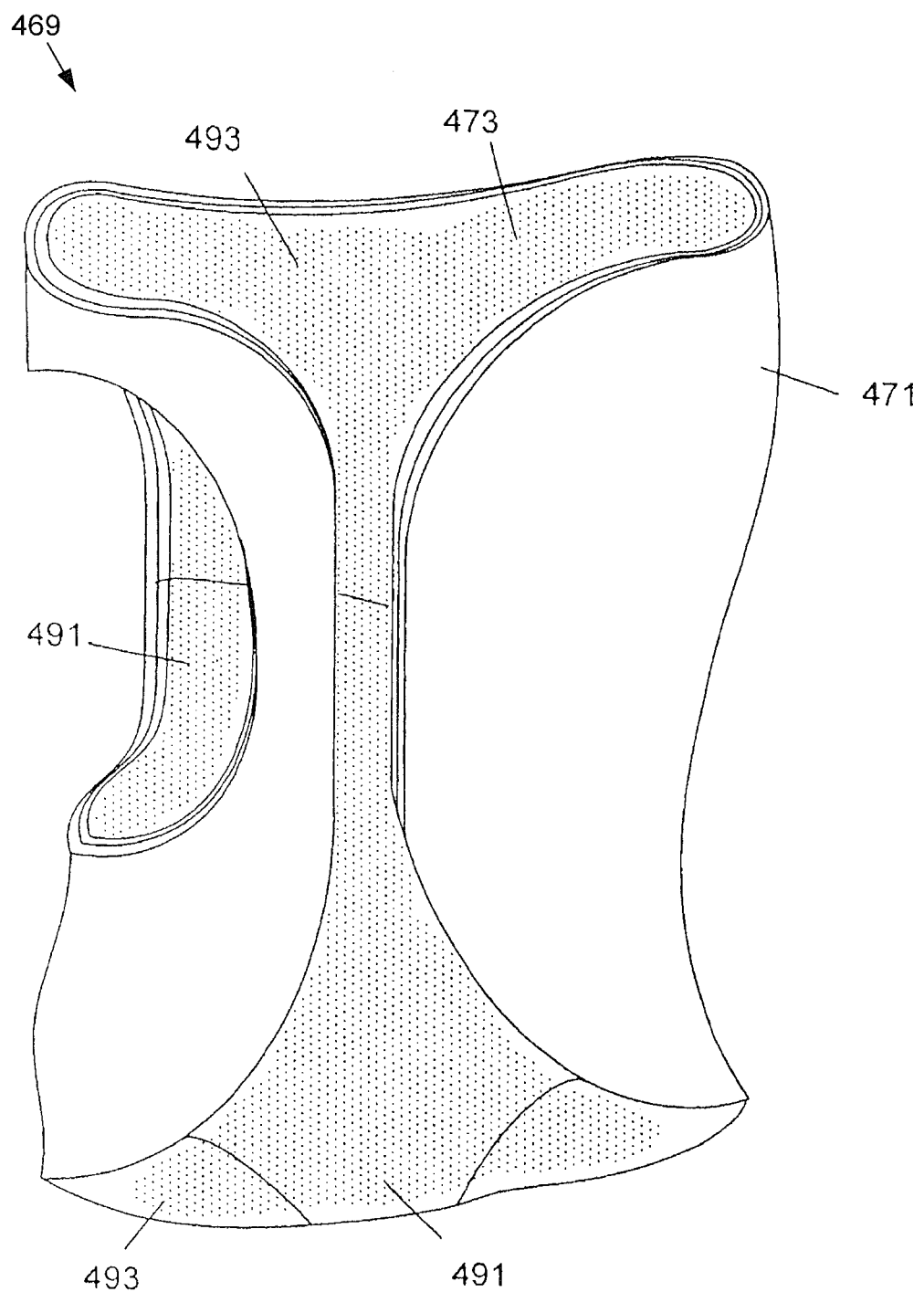
FIG. 39 illustrates a brace having a hard outer layer and a soft inner layer.

Thus, the brace can be designed as a homogeneous material or as a composite structure of laminated layers of materials as shown in FIG. 39. The outer layer 471 may be a very strong structure that functions as an exoskeleton that provides the required strength for the body or limb. While the inner layer (s) 473 of the brace 477 can be a combination of hard materials 491 and soft materials 493 that are designed to promote healing of the patient. Soft compliant materials 493 can be used over areas that are adjacent to bones. The position of the bone may change while the patient moves. Thus, it is important for this area of the brace to be comfortable. In contrast, harder materials 491 can be used against the softer fat and muscle tissue of the body. Because these softer internal surfaces can be damaged or may wear out sooner than the hard materials, they may be designed as replaceable panels or parts that snap in and out of the brace.

Figure 40:
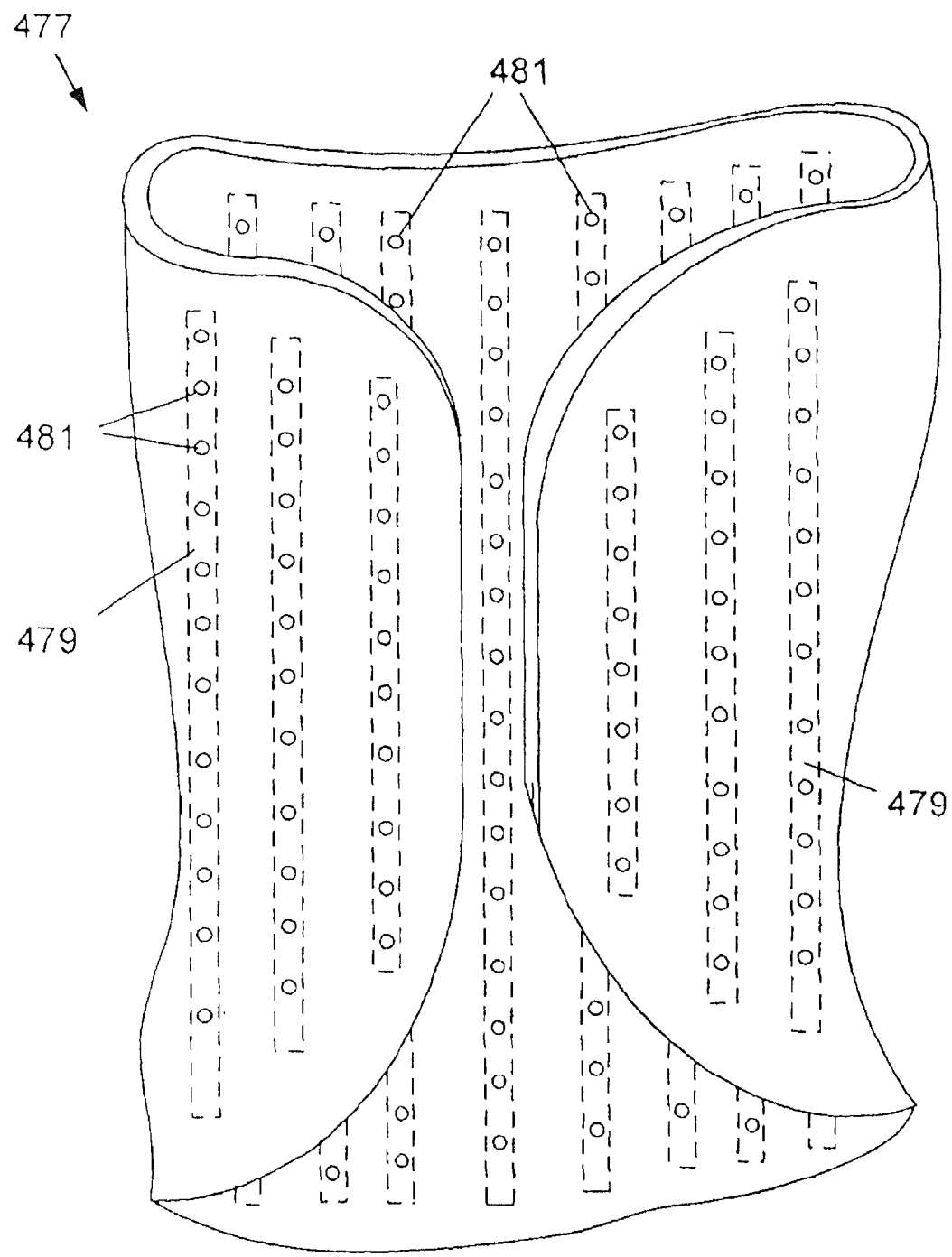
FIG. 40 illustrates a brace having internal ventilation passageways.

The breathability of the brace is another feature that makes the inventive brace more comfortable. With reference to FIG. 40, the brace can be designed with internal ventilation passageways 479 that extend throughout the brace 477. Because the brace 477 is designed on a CAD system, the locations of the ventilation holes 481 is known and can be automatically designed into any additional padding or panels that are placed in the brace 477. In some cases, the pads may be made of a breathable material and the ventilation holes in the hard solid portions of brace may provide ventilation to a much larger internal surface of the soft porous pad.

The brace design can also control the flexibility by combining both the vertically and horizontally orientations of the beams, a brace can feature difference areas of flexibility from one part to another, without compromising ventilation. In an embodiment, the beams of material are curved. For example, a portion of a brace can have more horizontally oriented beams on a first side, and more vertically oriented on a second side. In this manner, the first side will be more likely to compress and expand under pressure, while the second side will not. The second side, by contrast, will more likely bend and act as a pivot. If, for example, the front of the body features more horizontally-oriented beams and the sides feature more vertically oriented beams, then the brace would allow forward flexion, though deny any lateral flexion. At the same time, however, ventilation would be equally uniform throughout the brace. This illustrated configuration can be applied to a back brace that allows bending forward but prevents side to side bending. The left side can represent the front of the brace and the right side can represent the right side of the brace. The horizontal alignment of the beams in the front and the vertical alignment of the beams at the side allow forward rotation but prevent side to side rotation.

Figure 15:
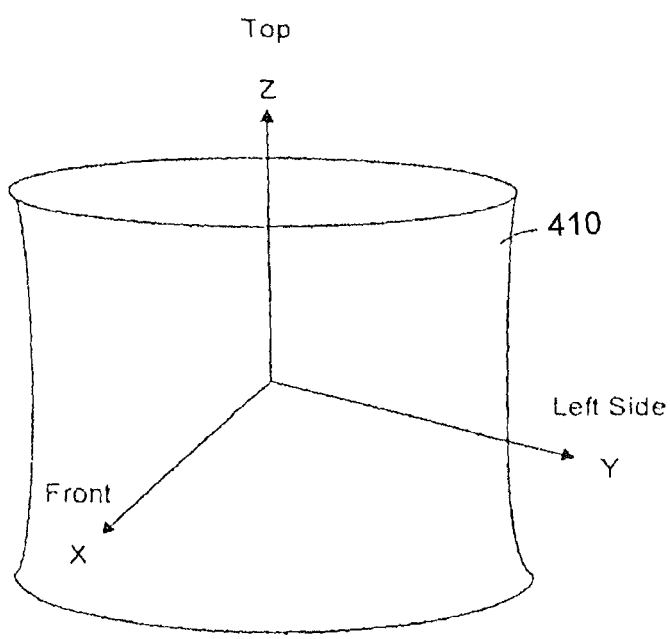
FIG. 15 illustrates a brace and rotational axis.

A basic principle of the brace invention is the asymmetric flexibility of the brace. With reference to FIG. 15, the brace 410 is shown in terms of an XYZ coordinate system with the front of the brace facing the X axis, the left side facing the Y axis and the top facing the Z axis. In this example, the brace 410 is a back brace and the lower portion of the patient and brace 410 are stationary. If the patient leans to the left, the brace 410 will bend clockwise about the X axis and if the patient leans to the right, the brace 410 will bend counter clockwise about the X axis. If the patient bends forward, the brace 410 will bend counter clockwise about the Y axis and bending back will cause the brace 410 to rotate clockwise about the Y axis. If the patient twists to the right, the top of the brace 410 will rotate clockwise about the Z axis and twisting to the left will cause the top of the brace 410 to rotate counter clockwise about the Z axis. By knowing which directions to immobilize the patient's movements, the brace 410 can be asymmetrical in bending.

With reference to FIGS. 16-18, different views of a back brace 510 are illustrated. FIG. 16 illustrates a front view of the brace 510, FIG. 17. Illustrates a side view and FIG. 18 illustrates a back view. The brace 510 can be configured with horizontal beams 505 on the front section and the front portions of the left and right sides. Because the spine should not be compressed, the back of the brace 510 may include vertical beams 507 while does not have vertical beams. Because the back is stiffer than the front, the back will tend to bend but not compress. In contrast, the front will compress or expand in response to the bending of the back. Because the vertical beams 507 are mounted across the width of the brace 510, they can prevent the brace 510 from bending from side to side. While the brace 510 has vertically and horizontally aligned beams, these only represent the general alignment of the beams. The beams of the actual brace will cross each other and be angled or bent to provide the required directional strength and flexibility.

Figure 21:
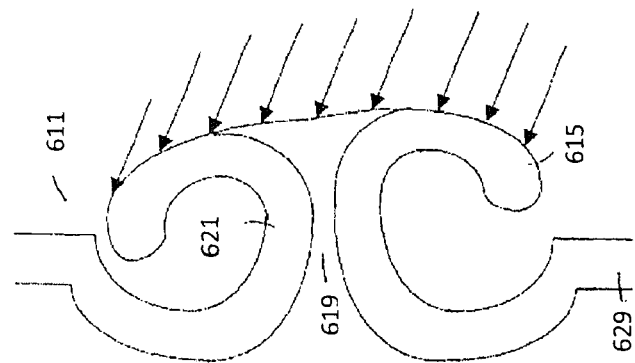
FIGS. 19-21 illustrate cross sectional views of a pad for a brace.
Figure 20:
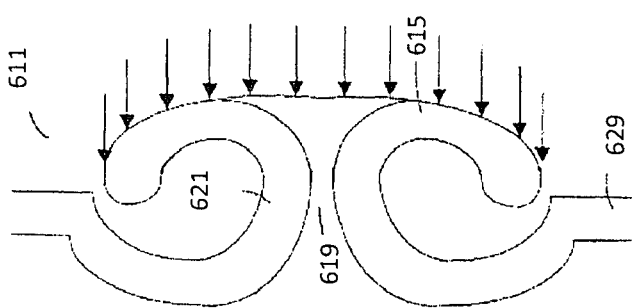
Figure 19:
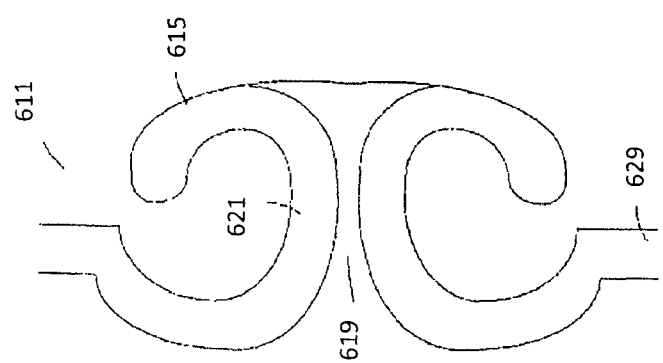

With reference to FIGS. 19-21, another feature that can be designed into the brace is a dense grid of individually suspended contact pads 611 involves each pad 611 being 'hollow', giving it the shape of a torroid. This allows contact 'rings' 615 to contact the skin, each contract pad 611 can have a ventilation hole 619 at the center. The ventilation holes 619 gives improved airflow to the skin. The 'doughnut' shape of it makes window edema less likely, since there are no hard edges to press against the skin to disturb the blood flow. And the relatively large contact pad 611 area will likely increase the comfort against the skin. Air will also flow around each of the contact pads 611, and can be evacuated through a perforation pattern through the outer wall. This will increase comfort to the user and cool the surface skin temperature.

Because each of the contact pads 611 may be created as an individual revolved 'cell', it can be created so that a 'well' exists around each of the pad's 'stocks'. Beyond the 'well', the wall thickness grows, since the thick parts of the cells intersect adjacent cells. This allows a relatively strong structure to be created that is flexible where desired (around the stocks of each pad), yet strong where desired (in between each stock). Both strength and compliance is met in a single surface. This contact point on a stalk approach distributes the skin contact over many individual points. These point contacts minimize the area of decreased circulation by allowing blood flow to the skin between the contact points. The compresses area can thus receive blood supply by diffusive processes. This strategy minimizes the potential for larger ischemic zones or areas of skin breakdown. In addition, by varying the mechanical properties of the stalk that supports the contact point the amount of shear stress at the skin can be minimized. If the stalk is sufficiently flexible, with motion of the skin within the brace, motion will not occur between the contact point and the brace but instead will occur at the level of the stalk, between the contact pads and the exoskeleton outer layer of the brace. By minimizing shear and ischemia, such a padded structure can minimize the potential for skin breakdown.

For dynamic braces, these contact pad 611 constructs can be produced as a coherent volume of attached structures, or for more dynamic braces, the contact pads 611 may be printed as discrete elements in continuity with the outer exoskeleton and ventilation pattern, but whereby the contact pads 611 and support structure exclusive of the exoskeleton are not in contact. Such a construct would allow for differing motions in select regions of the brace without any impact on the mechanical properties due to the contact pads.

The pads 611 illustrated in FIGS. 19-21 are part of the inner surface of the brace. Each pad 611 is flexible and movable in compression as well as horizontal movement. In an embodiment, the pads 611 each have a contact portion 615 and a stem 621 that is coupled to a frame. When the pad 611 is compressed against a portion of the patient's body, for example when the brace is worn by the patient, the contact portion 615 is compressed against the stem 621 which is compressed against the frame 629. The stem 621 can be much narrower than the contact portion and bendable. When the contact portion 615 of the pad 611 moves horizontally, the stem 621 will bend in response to the pad 611 movement. The stem 621 is also coupled to the frame 629 in such a way that the stem 621 can move in a perpendicular direction relative to the plane of the frame 629. Thus, the pad 611 can move in response to any perpendicular compression of the pad 611 against the frame of the brace. In an embodiment, a portion or the entire interior surfaces of the brace can include the described pads 611. The pads 611 used in a brace can all be identical or each can have a different design characteristics. For example, the pads 611 located over harder surfaces such as bones under the skin can have flexible pads 611 that allow for comfortable movement of the bones and/or joins. In contract, the pads 611 that are located over softer areas of the body can have stiffer since the soft areas may not require as much padding. FIG. 19 illustrates a cross section of an example of a single pad 611 element. FIG. 20 illustrates the pad 611 in direct compression and FIG. 21 illustrates the pad 611 in diagonal compression. In the compressed illustrations, the stem 621 bends in response to the pressure applied to the pad 611.

In other embodiments, different flexible pad designs can be used including non-circular surfaces, different spring stems and different ventilation mechanisms. The hardness or softness of the pads can be quantified by the spring rate of the stem against the frame and the contact area of the pad. A pad with a large contact area and a low spring rate will be very soft. In contrast, a pad with a small contact area and a high spring rate will be a harder pad. The equation quantifying the hardness or softness of the pads is (pad surface area)×(stem spring rate)=X. For example, if the pad area is 1 square inch and the spring rate is 10 lb per inch, when the pad is compressed ¼ inch into the frame, the force will be 2.5 lbs per square inch. If the pad is compressed ½ inch into the frame the force will be 5 lbs per square inch. The dynamic hardness/softness characteristics of each of the pads can be individually designed into the brace. The pad areas can range from about ¼ square inch to about 5 square inches and the spring rate of the stem can range from about 0.01 lb/in to about 100 lb/in or more.

Figure 22:
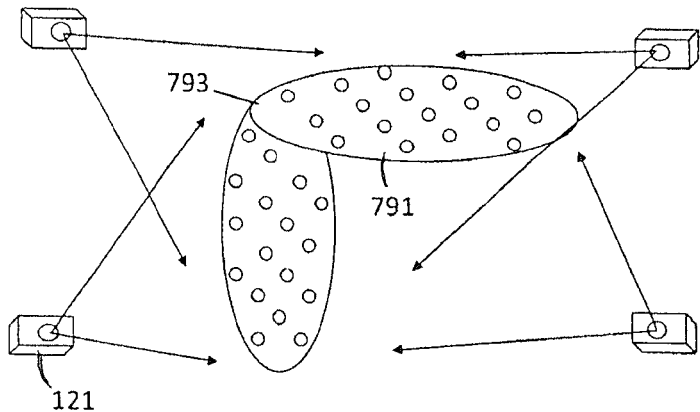
FIGS. 22-24 illustrate images of a leg captured at different bending angles.
Figure 23:
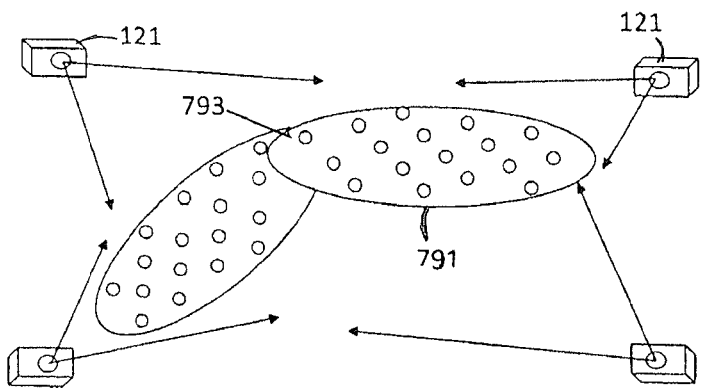
Figure 24:
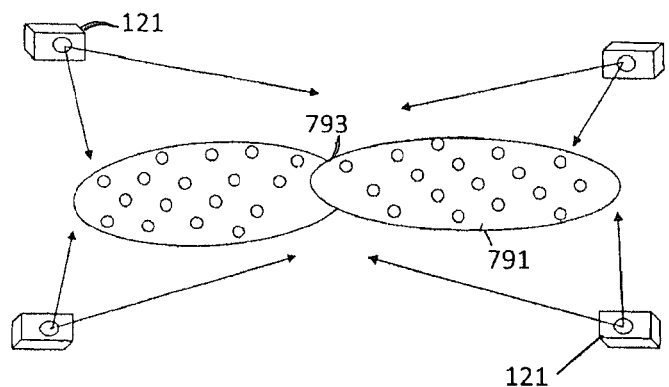

Other features that can be added to the brace design include hinges that allow the brace move at a joint or opened to be more easily attached to the body and removed from the body. The hinge can be located at a joint such as the user's knee or elbow to enables the brace to move with the knee or elbow joint. In order to determine the proper orientation of the hinge, a series of photographs of the limb can be taken at different joint angles. For example with reference to FIG. 22, a first set of photos can be taken of the leg 791 with the knee bent with one or more cameras 121. With reference to FIG. 23, a second set of photos can be taken with a slight bend in the knee 793 and with reference to FIG. 24, a third set of photos can be taken with the knee 793 straightened. By using the cumulative data, the designer can determine surface coordinates for each leg 791 position and the most accurate location for the hinge. The elbow or knee does not move in perfect rotation about a fixed axis, however the designer can determine the closest fit rotational axis for the brace. Once the best rotational axis is determined, the designer can integrate a hinge into the brace design.

Figure 25:
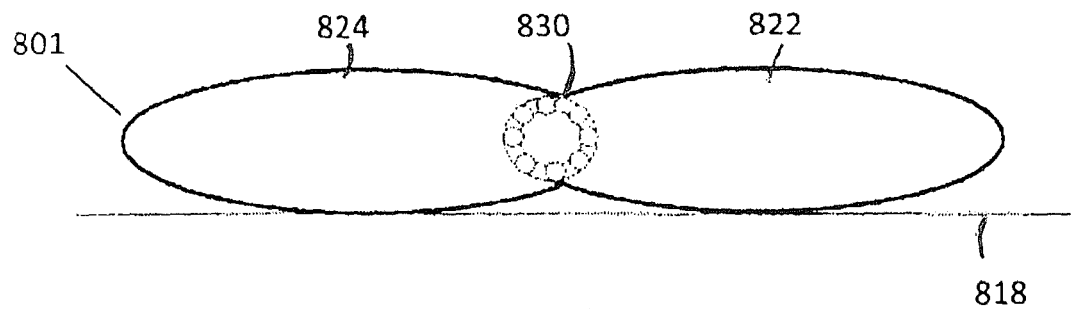
FIGS. 25-27 illustrate views of a leg brace.
Figure 26:
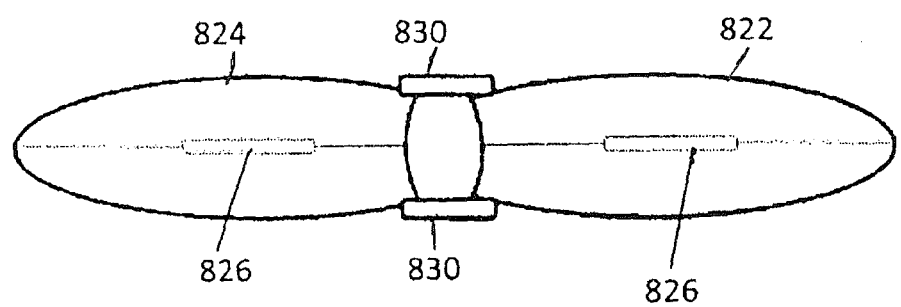
Figure 27:
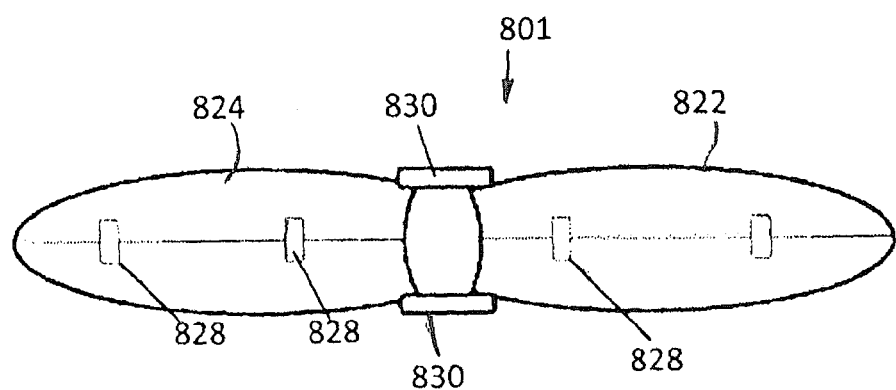

With reference to FIGS. 25-27, the hinges 830 can be a circular structure that couples the upper portion 822 and lower portion 824 of the brace 801. In an embodiment, the upper portion 822 and lower portion 824 are connected by two hinges 830 mounted on opposite sides of the brace 801 and define an axis of rotation. The hinges 830 can include bearing structure that minimizes the rotating friction of the hinge 830 and allows for smooth movement of the upper portion 822 and lower portion 824. The bearing 830 can include an inner race and an outer race. The inner race can have a bearing surface that extends around the outer diameter and the outer race can have a bearing surface which extends around the outer diameter of the race. Bearings such as ball bearings, roller bearings, etc are mounted between the races. The bearing materials can be metal, ceramic, plastic, etc. With the surface coordinates, a designer can integrate the bearing structures into the design of the brace.

In order to insert and remote the limb, the brace 801 can have an opening mechanism(s) that allows the user to easily insert and remove the limb. For example, the brace 801 may be split along the length and divided into two or more portions that are coupled together. In order to insert the limb, the entire brace can be open and after the limb is inserted, the brace portions 822, 824 can be secured around the limb. In an embodiment, the brace 801 can have a hinge 826 on one side and a latch mechanism 828 on the opposite side. The latch mechanism 828 can be released so the brace 801 can be opened. In order for the opening hinge(s) to function properly, it must be aligned along the length of the brace 801. More specifically, if the brace 801 includes a hinge 826 for the elbow or knee, the hinges 826 coupled to the upper portion 822 and lower portion 824 must be aligned so the brace can be opened. In an embodiment, the opening hinges 826 are aligned when the upper portion 822 and lower portion 824 of the brace 801 are aligned. Thus, the brace 801 may only be open when the upper portion 822 and lower portion 824 are aligned.

When the outer surface coordinates have been obtained, the inner surfaces of the brace can be designed to match the outer surfaces of the limb. This provides a brace or cast that perfectly matches the injured limb. The matching surfaces allow the brace or cast to have a more accurate and comfortable fit. The designer can also determine a thickness of the brace that is sufficient to support and protect the limb. The designer can split the brace into two pieces along the length so that the brace can be opened and the patient can insert or remove the limb.

With reference to FIGS. 25-27, the system can also determine the best locations for hinges 826 that extend along the length of the brace 801. Because the outer surface is not straight, the hinge 826 may only be mounted at the outermost portions of the brace 801 along a straight line. In an embodiment, the computer design software will locate a preferred hinge 826 location that may extend along the longest line that is within a short distance of a straight line that is at the back of the leg. This configuration allows the latches to be mounted on the front of the leg which allows the brace or cast to be more easily removed or attached. For example, the longest straight line at the back of a leg brace may be at the back of the calf area of the leg. The design system will integrate a hinge along a line that extends along the back of the calf area that is within a predetermined distance, such as ½ to 1 inch, from the line. The design system can fill in the gap between the hinge and the curvature of the brace with filler material. A closure mechanism can be coupled to the opposite side of the brace which can be a latch, clamp, ratchet, or other closure mechanism. The closure mechanism may be adjustable so that the interior volume of the brace can be variable. The closure mechanism can be clamped tight so that if the limb gets smaller due to atrophy, the brace can also be made smaller to maintain a proper fit. The brace can also be expanded if the limb gets larger due to increased muscle size or swelling.

In an embodiment, the arm or leg brace includes an upper and a lower portion that move about knee hinges or bearings relative to each other. In this embodiment, the opening mechanism can include an upper and lower hinge that are each coupled to the upper and lower portions of the brace 801. The designer can align the upper portion 822 and lower portion 824 of the brace 801 with a straight line 818 as shown in FIG. 25 and then insert the straight hinge 826 at the intersections of the brace 801 and the straight line 818 as shown in FIG. 26. In this example, the hinge 826 has two sections that are axially aligned. Thus, the upper portion 822 and the lower portion 824 must be aligned to open the brace 801. Along the opposite side of the brace 801, the design system can insert one or more coupling mechanisms 828 that will hold the brace together as shown in as shown in FIG. 27.

Figure 28:
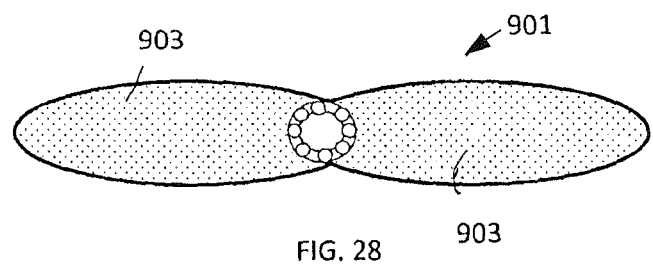
FIGS. 28-29 illustrate views of a leg brace with ventilation holes.

Another problem with existing casts is that they do not allow air to circulate against the limb. This can be uncomfortable because the limb is not easily cleaned and the dead skin is not removed. In order to allow for some air circulation against the limb, the brace or cast can be designed with ventilation holes that can be distributed over the surface of the brace. Many small holes 903 can be distributed over the entire cast or brace 901 and extend between the inner and outer surfaces as shown in FIG. 28. This allows the brace or cast 901 to be structurally very strong, but still allow for air to circulate against the skin. The inner surface may also have channels or grooves in the surface that allow air to flow against the skin.

Figure 29:
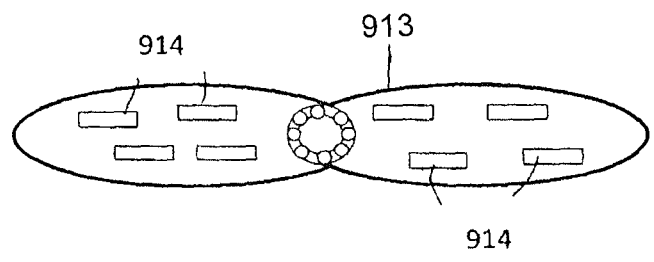

In other embodiments, larger holes 914 may be formed in the brace or cast 913 as shown in FIG. 29. Since these areas under these larger holes 914 will not provide support or protection, the larger holes can be positioned over less critical areas of the brace. For example, a leg brace may be used to protect the knee. Thus, the ventilation holes should not be located in areas that the brace is intended to protect. In addition to functional purposes, the holes or any other ornamental, identification, or other features can be built into the brace or cast design.

Figure 30:
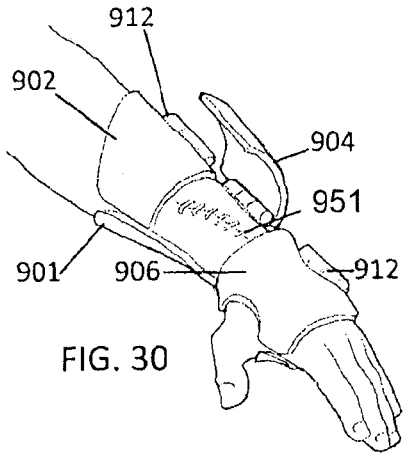
FIGS. 30-31 illustrate brace having accessible regions.

With reference to FIG. 30, in an embodiment, the brace 901 can have a plurality of accessible regions 902, 904, 906. The access regions 902, 904, 906 can be large or small depending upon the injury and patient. The different regions 902, 904, 906 may be marked on the patient prior to photogrammetry.

Figure 31:
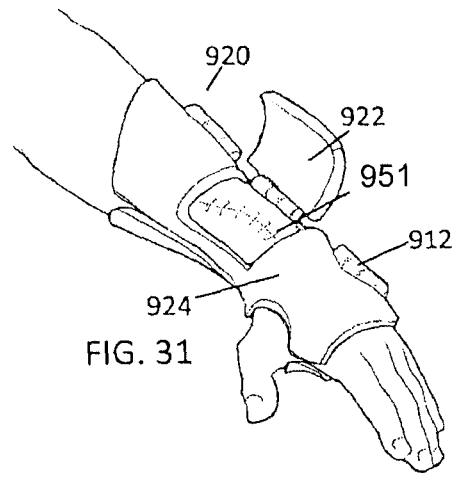

Each access region 902, 904, 906 can be attached to a hinge 912 or other releasable fastener that allows the individual portions of the patient covered by the brace 901 to be accessed. The access regions 902, 904, 906 can be strategically placed over a specific area of interest, for example a wound area that needs to be cleaned or periodically checked. In other embodiments, the access regions 902, 904, 906 can also extend along the entire length of the brace 901. The entire limb or body area covered by the brace 901 can be accessed for cleaning, inspection, removal of stitches 951 or other reasons by opening each region 902, 904, 906 individually while the rest of the limb or body is protected and immobilized by the brace 901. With reference to FIG. 31, in another embodiment, the brace 920 can have an individual access region 922 and the rest of the upper portion 924 of the brace can be coupled together.

With reference to FIGS. 32-37, in an embodiment, the brace 930 can be a modular design that can have a modular construction with modular sections that can be completely removed from the brace 911. This design can be useful for a broken limb bones such as a forearm. Casts are well known in the medical art. When a bone is broken, the bones can be set to reduce the size of the fracture and a cast is placed around the hand, lower arm and upper arm. As the arm heals, the casts are removed and replaced with smaller casts. A patient can go through several cast replacements depending upon the type of break. This can be very time consuming because each cast must be sawed off and a new shorter cast must be constructed over the arm or leg. Also as discussed, the application and removal of casts with a cast saw can be very traumatic to children who may need to be sedated during these procedures.

In an embodiment, a modular brace 930 can be designed for a patient that can have several modular sections including: an upper arm 940, cuff 942, elbow 938, lower forearm 932, upper forearm 934 and thumb spica 936. The sections can be removed sequentially as the patient heals. The patient can be marked at the junctions between the different module sections. The markings are detected by the photogrammetry process and the different module sections are designed into the brace 930. Because x-rays are normally taken of broken bones, this x-ray data can be viewed with the photogrammetry images and the brace 930 can be designed with the required structural integrity to protect the arm at the damaged areas of the body. The brace 930 is designed as described and the modular sections can be secured to each adjacent section by removable fastener such as screws or any other type of couplings that are formed in the brace or attached to the modular sections.

With reference to FIG. 32, if a patient breaks an arm, the entire arm may initially be immobilized with a brace 930 that extends from the fingers to the shoulder. With reference to FIGS. 33A and 33B, after a first period the cuff 942 can be removed from the upper arm module 940. This allows the elbow to flex after a period of isolation. If the cuff 942 is hinged to the upper arm module 940, the coupling can be opened. Alternatively, the cuff 942 can be coupled to the upper arm module 940 with a hook and loop fastener, Velcro and may be un-Velcro-ed to remove the cuff 942. With reference to FIG. 34, after a second period, the entire upper arm module 940 can be removed when appropriate for treatment to allow the elbow flexion. An elbow module 938 still exists which surrounds the elbow and allows flexion, but does not allow for rotation.

Figure 35:
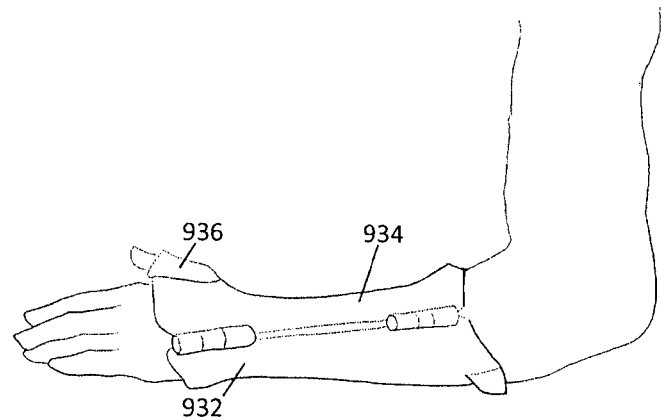
Figure 36:
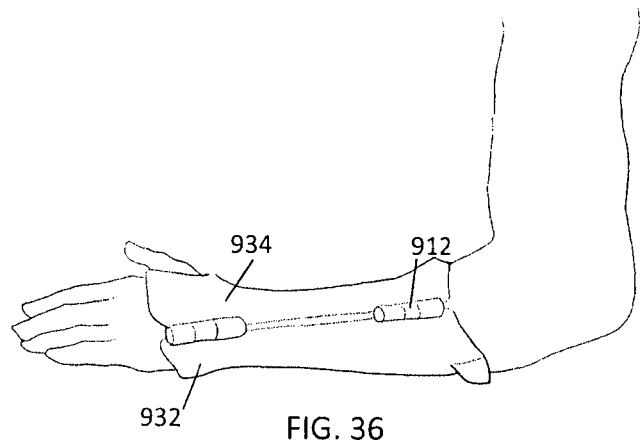
Figure 37:
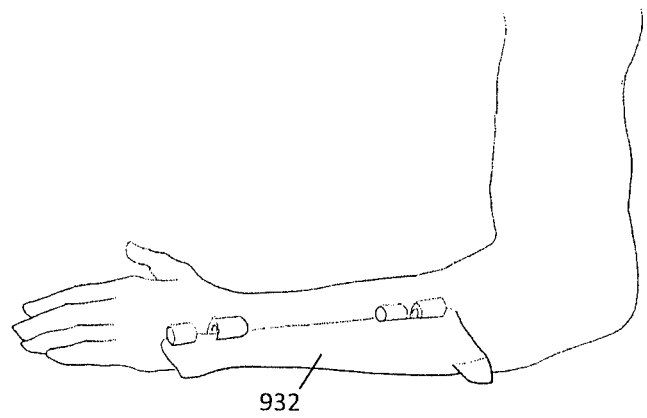
FIG. 37 illustrates a section of a brace used to stabilize the arm.

With reference to FIG. 35, the elbow module 938 is removed leaving a 'short arm' cast for the remainder of the treatment. This upper forearm 934 can be coupled to the lower forearm 932 with a hinge 912 and may be opened temporarily for cleaning of the skin and inspection, though it will close in order to keep the arm stabilized during the treatment. With reference to FIG. 36, the 'thumb spica' 936 may be removed at any time during the treatment, allowing motion for the thumb. Finally, with reference to FIG. 37, lower forearm module 932 of the brace 930 may remain as a 'splint' that may be held in place by a Velcro strap if needed after treatment for additional stability and safety.

In other embodiments, a similar brace can be made for an injured hand, foot or leg. For example, when a patient injures a hand, the entire hand may initially need to be placed in a modular brace that includes different modules for the wrist, palm, fingers and thumb. The brace may also include access portions. The doctor can mark the area that is injured as well as the desired locations for each of the module seams and access location. The brace can then be designed and fabricated. The brace is then assembled with all of the modules and any required pads. As the hand heals, the individual modules can be removed from the brace and the patient can regain use of the hand. Eventually, only the damaged finger may need to be in a brace until the patient has fully recovered. Because the hand has many small components, it can be difficult to make and remove traditional hand casts. The inventive process greatly simplifies the recovery process because only one brace is required and the modules are simply removed as the patient heals.

Removing the modules at the designated time periods can be very important to the healing process. A joint that is left immobile for extended periods of time can become very stiff. Thus, it is important to make the joints active as soon as possible. The lower arm module 932 925 can continue to be worn to support the patient's arm until the injured bones completely heal. The inventive brace has many benefits over traditional cases. Since the modules are removed, new braces are not required. Since the braces modules are removable, the doctor can inspect the limb and the patient can clean the limb if necessary. The patient does not need to remain at the hospital after the injured limb is marked and photographed. A substantial amount of time is saved when each section is removed compared to having to periodically remove and replace the cast. Additional padding can be inserted into the brace if the limb shrinks due to atrophy. Finally, if the patient breaks the limb again, the custom modular brace may be reused if the limb has not changed significantly. In addition to being the proper dimensions, the brace or cast must also be strong enough for the required use. An ankle brace or walking cast may be required to support the user's weight and impact while running or jumping and an arm brace or cast must be able to withstand the normal use forces. In an embodiment, the strength of the brace or cast is determined by the geometry of the brace or cast components and the materials used to fabricate the components. Suitable materials include high strength plastics such as high strength polyamides metals, alloys and composites such as carbon fiber in an epoxy binder.

In another embodiment, markings on the skin can determine areas for padding of bony contours or areas for adding additional padding over time to maintain contour. Using this system, conforming pads can be printed by the same process to fit within the confines of "fitted regions" within the inner walls of the cast. An array of conforming surface pads of progressive thicknesses can be produced and provided to the health care provider with the initial cast. The inner conforming pads can be made of a softer flexible material that can be produced by additive manufacturing techniques.

The inner pads can have porosity that matches the ventilation holes of the outer exoskeleton for improved ventilation. The inner pads can have locking devices manufactured into the pads such that they snap into the correct location with the correct orientation. Alternatively, an adhesive can be used to attach the pads to the brace. Because both the pads and brace are custom made, they may be marked with locations indicators that can be text, color coding or symbols indicating where and possibly how the pad and brace should be attached to each other. For example, the text on the pad may state, "attach this pad to the upper back section of the brace by attaching the connector to hole A in the pad."

As the body heals, the lack of movement can result in atrophy which causes the body to shrink. Thus, the first set of pads may be the thin. When the brace or cast with the original thin no longer fits properly, the thin pads are removed and replaced with thicker pads. The array of conforming pads can include the different thicknesses that are expected to be needed. Since the digital design for the pads is stored, additional pads can be fabricated from the stored pad designs.

The CAD system can be used to design the load-bearing member of the brace or cast. In general, the cast or brace will be much stronger than required by the user. In an alternative embodiment, the designer can input the weight and activity level of the user into the CAD system and the required strength can then calculate based upon expected loads. The CAD system can then design a load bearing structure that will be able to support the load requirements.

The medical device can be designed as a single or multiple piece structure that is designed to be fabricated simultaneously through a rapid prototyping process. Alternatively, the medical device can be designed as a multiple piece structure that is assembled before use. This multiple piece construction can be more efficient in terms of fabrication. Rather than forming the brace as a single piece that is not space efficient, the brace can be fabricated from a plurality of flatter sections that are later assembled. When a brace is designed with a large open center volume, the fabrication machines produce the brace but the center volume is empty. The fabrication machines can operate at the same speed and cost if the center volume is empty or filled with other structures. Thus, by designing the brace as a plurality of flat sections, the components for one or more braces can be fabricated simultaneously in a more efficient manner. After the components are fabricated, they can be assembled to form the brace, for example, as illustrated in FIG. 10.

Once the design is finalized, the design data produced by the CAD system can be used to fabricate the brace or cast. Because the information for the brace or cast are in a digital format, the brace or cast can be fabricated anywhere. In a preferred embodiment, the fabrication takes place locally, so the patient can receive the brace or cast as quickly as possible. Alternatively, the patient can be in a remote location and the brace or cast design information can easily be transmitted electronically to a fabricator located in a more industrial area. The brace or cast can then be fabricated using the design data and shipped to the patient located in the remote rural location.

In the preferred embodiment, the brace or cast is fabricated through a rapid prototyping process that uses an energy beam directed at a bath of liquid or powdered material. Similar fabrication processes are known as additive manufacturing, rapid manufacturing, layered manufacturing, 3D printing, selective laser sintering (SLS), fused deposition modeling (FDM), stereo lithography (SLA), electron beam melting (EBM) and other methods. These fabrication processes use an energy beam that is deflected across the material and causes the exposed material to harden. Another possible manufacturing process is fused material deposition (FDM).

The cross section design data is used by the fabrication machine to construct the main or entire brace or cast assembly in a sequential series of layers. As each layer of material is hardened, the completed portion of the custom cast, brace or device component is moved vertically into the bath and the next cross section layer is formed and fused to the adjacent formed layer. When all layers are formed, the custom cast, brace or device component is completed. The structure can be a single piece or assembly of multiple pieces may be required to complete the device. Because the fabrication process can be precisely controlled to create sliding surfaces, even the hinged portions can be fabricated simultaneously with the other portions of the cast or brace.

In an embodiment, the brace or cast is fabricated as a single integrated structure so that the finished product is complete. As discussed above, the moving components of the inventive brace or cast can be coupled to a knee or elbow or opening hinge having rotating components. For example, the opening hinge may have bearing components that have require rods that rotate within holes. The rapid prototyping method can simultaneously produce the rods and corresponding holes.

In other embodiments, additional components can be added to the cast or brace so that the components do not slide against the same material. In an embodiment, bushings or bearings can be added to the brace or cast at the points of rotation. The bushings may be made of lubricious materials such as, stainless steel, ceramic, Delrin or Teflon. In other embodiments, bearings are used. The bearings may be sealed units with roller, needle, ball bearings or any other type of bearing. The bearing material may be ceramic, metal or plastic. Known mechanisms may be used to retain the bushings and/or bearings between the sliding surfaces.

In another embodiment, the surface data of the body or injured limb can be obtained through another scanning process and input into the CAD program. For example, the body or limb can be scanned with a three-dimensional optical scanner. The body or limb must be scanned from multiple sides to obtain a full three dimensional digital image. The scanner creates a data set of geometric measurements for many points on the surface of the body or limb. The accuracy and detail of the three dimensional digital image is improved by taking more measurements of the body or limb. Suitable handheld laser scanners include the FastSCAN system by Polhemus and the Handyscan 3D system by Handyscan. The drawbacks of optical scanners is that they may not only detect the surface of the body and not the markings placed on the patient. Also the scanning can take a substantial amount of time because, the optical beams may need to be moved over the entire body of the patient. The patient must also remain very still during the scanning process. As discussed, this stillness can be extremely difficult without sedation of infants or animals. Because of these drawbacks, photogrammetry is the preferred method for obtaining the surface and marking data for the patient.

The scan data is converted into a usable surface file that can be read by the CAD program. More specifically, the surface data from scan of the body or limb may be referenced in order to extrapolate the shape of the body or limb through a reconstruction process. The reconstruction process uses an algorithm that connects the adjacent points, known as a point cloud, with lines from the scanned body or limb data to construct a continuous surface from many small polygon shapes that form a polygon model. The data produced by the reconstruction process is a continuous three dimensional digital representation that closely matches the surface of the body or limb. An example of the software used to perform the scanner data reconstruction process is Geomagic Studio by GeoMagic and Pro Scan Tools which is a plug in module for Pro/Engineer by Parametric Technology Corporation. The reconstruction surface file for the body or limb is input into the CAD program for the cast or brace design.

In an embodiment, the components or an articulating brace are fabricated simultaneously using a rapid prototyping machine. While the parts can easily be fabricated simultaneously, it can be difficult to create parts such as the knee joints mounted on opposite sides of the brace. In an embodiment, the knee joint has a ball bearing construction that can be installed as an integrated or modular mechanism. Rather than fabricating the races and the ball bearings simultaneously, the joint can be fabricated with just the bearing races. After fabrication, the bearings can be inserted between the race components. The bearings provide a smooth sliding mechanism and also tighten the fit between the sliding components. If the bearings wear out, they can be replaced so the leg brace can be repaired. Alternatively, the bearings can be a modular design that can be removed and replaced when worn out. In yet another embodiment, the joint can be a sliding modular bushing that can also be replaced when it has worn out.

As discussed, the photogrammetry can detect other markers used to indicate additional information about the patient to the brace designer and CAD software. The axis of rotation of the knee can be determined and indicated prior to obtaining images of the knee. For example, an elongated rod or any other marker indicating an axis can be placed on either side of the knee to indicate the axis of rotation. The rod or marker will be detected and the CAD software will interpret this marker as indicating the axis of rotation. Alternatively, it may also be possible to derive the axis of rotation based upon multiple images of the knee taken at multiple bending angles as illustrated above with reference to FIGS. 22-24. Similar markers can be used to indicate the axis of rotation of any other joint that is needed in a custom brace or device.

Because the range of motion is controlled by the joint, it is possible to limit the range of motion by using stops in the knee joint of the leg brace. In an embodiment, the stops can be variable and adjustable as the patient heals. Initially, the range of motion can be limited to a narrow movement. As the patient heals, the range of motion can be expanded until the patient regains the full range of motion for the limb and/or body. In an embodiment, an elastic resistance mechanism can be applied to the ends of the range of motion. Thus, the last predetermined angular motion can be resisted by an increasing elastic spring force. Like the stops, the elastic region is variable and will normally be expanded as the patient heals.

In an embodiment, the CAD system can include a graphical user interface (GUI) that allows the designer to easily change the appearance of the brace or cast. The GUI may be a special, custom, proprietary application, or it may simply be a CAD model that is built inside Pro/E. The GUI can have controls that allow the brace or cast to be viewed with a specific color that preferably matches the user's skin color but may also be any other color.

When the designer completes the designs of the brace or cast, the design data produced by the CAD software can be used to create a unique and custom fabricated the brace or cast. Rapid prototyping is a general category of systems that uses digital design data and software to fabricate the components from various types of materials including metals and plastics. These machines most often use an energy beam that is deflected across a bed of liquid or powdered material. The exposure to the energy beam causes the material to fuse together and harden. These fabrication machines are able to create all custom cast or brace components.

In order to fabricate the cast or brace components with the rapid prototyping machines, the CAD design data may need to be modified. The normal CAD design data for a component is converted into many parallel cross sections of vector data that extend along the length of the component. The data transmitted between the CAD software and the fabrication machine approximates the shape of the component cross sections through many connected triangular facets. Smaller facets produce a higher quality surface but require more time to calculate and can create very larger manufacturing data sets. The output of the CAD design program can be a standard STL file that is an export option, similar to a JPG export or any other file format.

The vector data for the component cross sections is read by a rapid prototyping scanner controller that converts the vector data to movement information which is sent to the energy beam scanhead. In a laser beam embodiment, the rapid prototyping machine includes a scanhead having two mirrors that deflect the laser beam in the X and Y coordinates over a bath of liquid or powder material. The fabrication information is then used to control the print head cross section to create each component cross section successively. The scanhead controller reads the fabrication data and causes the print head to expose successive layers of liquid, powder, or sheet material to precise patterns of laser light. Once the layer is completely formed, the component is moved into the bath so a thin layer of the material covers the previously formed layer. The process is repeated many times with new layers formed and fused to the previously formed layers. In an electron beam embodiment, an electron beam is deflected over a bath of material in the X and Y coordinates with magnetic fields. The component cross sections are sequentially formed until the component fabrication is completed.

The primary advantage to additive fabrication rapid prototyping is the ability to create very complex shapes and geometric features. A light weight and strong cast or brace can be made with a rapid prototyping machine from plastic materials such as photopolymers. An additional benefit of rapid prototyping is the ability to create complex, interlinked and assembled parts in one run. In contrast, traditional means used by the prior art required the individual manufacture many parts, followed by an assembly of the parts. Thus, the assembly can add significant costs, even though the individual parts may themselves cost very little to produce.

The rapid prototyping process can be applied to various materials including thermoplastics, photopolymers, metal powders, eutectic metals, titanium alloys and other materials. Because the inventive cast or brace is intended to be inexpensive, the preferred material is a thermoplastic material. Examples of some suitable rapid prototyping machines include: laser sintering machines by EOS GmbH, electron beam sintering machines by Arcam AB and laser stereo lithography machines and selective laser sintering machines by 3D Systems Corp. Similar fabrication processes are known by the names: additive manufacturing, rapid manufacturing, layered manufacturing, 3D printing, laser sintering, electron beam melting (EBM), etc. All of these fabrication processes use a similar operating principle of scanning an energized beam over a bath of material to solidify a precise pattern of the material to form each layer until the entire component is complete.

Another possible fabrication process is fused material deposition (FDM). FDM works on an "additive" principle by laying down material in layers. A plastic filament or metal wire is unwound from a coil and supplies material to an extrusion nozzle which can turn on and off the flow. The nozzle is heated to melt the material and can be moved in both horizontal and vertical directions by a numerically controlled mechanism, directly controlled by CAD software. In a similar manner to stereolithography, the model is built up from layers as the plastic hardens immediately after extrusion from the nozzle.

The inventive brace or cast can be fabricated in a sequential process. It an embodiment, a patient's limb or body part can be marked with reference points and photographed. The photos are processed and the reference points are triangulated to create the 3-D surface data file for the limb. The photos may include data for the limb in various positions and the photos may be used to determine a location of the moving knee or elbow. The designer can add additional features such as the opening hinge, the closure mechanisms, ornamental features, a knee or elbow rotational mechanism to the brace or cast and the final design is then converted into an electronic data file. The brace or cast data file is transmitted to a rapid prototyping machine which creates the brace or cast, possibly in a single fabrication process from a photopolymer material. Any additional components are required such as bushings, bearings or foot sole inserts, can be installed at the fabricators facilities. The completed brace or cast is then delivered to the end user. Since digital data can be transmitted on digital media via mail, electronically via cell or satellite, the inventive process greatly improves the design, fabrication and distribution of braces and casts.

It will be understood that the inventive system has been described with reference to particular embodiments, however additions, deletions and changes could be made to these embodiments without departing from the scope of the inventive system. For example, the same processes described for designing and fabricating a body or limb brace can also be applied to the design and construction of: shoulder spica, hip spica, spica casts, Pavlik brace, clubfoot casting, metartus adductus casting, Blounts disease casting/bracing, ankle foot orthosis, pediatric ankle casts, pediatric walking casts, spine-TLSO braces, halo body cast, cervical collar, torticollis bracing and other medical devices. In other embodiments, it is possible to use the inventive process for other products used by humans including: custom chairs, seats, saddles, athletic equipment, shoes, padding, helmets, motorcycle and bicycle seats, handlebars and hand grips, etc. The described apparatus and method can also be used for braces and casts for animals and custom saddles for horses and equestrians. The described apparatus and method can also be used for other applications including: automobile body repair and repair or reconstruction of other objects that require the reproduction of a surface contour. In an embodiment, the inventive process can be used to repair or replace sculptural and specially designed items such as jewelry. These items can be produced by the artist and then photographed and the digital representation can be stored. If the items are damage, lost or broken, the digital data can be used to make molds to reproduce or repair the objects. Although the custom casts, braces and devices that have been described include various components, it is well understood that these components and the described configuration can be modified and rearranged in various other configurations.

What is claimed is:

1. A brace comprising:
   an inner surface that corresponds to a digital representation of a portion of a patient's body;
   a structural layer of a material that surrounds the inner surface and holds the inner surface in a shape corresponding to the digital representation of the portion of the patient's body;
   an outer surface; and
   a first plurality of slots through the structural layer that are arranged in a plurality of rows, the slots in each of the rows are offset relative to the slots in adjacent rows with short strips of the material at ends of the slots in the rows intersecting center portions of the slots in the adjacent rows, the first plurality of slots gives the brace a first limited directional flexibility.

2. The brace of claim 1 further comprising:
   a second plurality of slots in the structural layer that gives the brace a second limited directional flexibility that is different than the first limited directional flexibility that is limited.

3. The brace of claim 2 wherein the first plurality of slots are in a first region of the brace and the second plurality of slots are in a second region of the brace that is different than the first region of the brace.

4. The brace of claim 1 wherein the first limited directional flexibility allows the brace to bend.

5. The brace of claim 1 wherein the brace at least partially surrounds a vertical axis and the first plurality of slots are not aligned with the vertical axis.

6. The brace of claim 1 wherein the first limited directional flexibility is non-uniform and the brace allows for bending in a first direction and resists bending in an opposite direction.

7. The brace of claim 1 wherein the first plurality of slots are substantially horizontal relative to a vertical axis.

8. The brace of claim 1 wherein the brace at least partially surrounds a vertical axis and the first plurality of slots are aligned with the vertical axis.

9. The brace of claim 1 wherein the first plurality of slots are substantially horizontal relative to a vertical axis.

10. A brace comprising:
    an inner surface that corresponds to a digital representation of a portion of a patient's body;
    a structural layer of a first material that surrounds the inner surface and holds the inner surface in a shape corresponding to the digital representation of the portion of the patient's body;
    an outer surface; and
    a first plurality of slots through the structural layer that are arranged in a plurality of rows, the slots in each of the rows are offset relative to the slots in adjacent rows with short strips of the material at ends of the slots in the rows intersecting center portions of the slots in the adjacent rows, the first plurality of slots gives the brace a first limited axial rotation flexibility.

11. The brace of claim 10 wherein the first limited axial rotation flexibility allows the brace to rotate.

12. The brace of claim 10 wherein the brace at least partially surrounds a vertical axis and the first plurality of slots are not aligned with the vertical axis.

13. The brace of claim 10 wherein the first limited axial rotation flexibility is non-uniform and the brace allows for axial rotation in a first direction and resists bending in an opposite axial rotation direction.

14. The brace of claim 10 wherein the first plurality of slots are substantially horizontal relative to the vertical axis.

15. The brace of claim 10 wherein the brace at least partially surrounds a vertical axis and the first plurality of slots are aligned with the vertical axis.

16. The brace of claim 10 wherein the first plurality of slots are substantially horizontal relative to a vertical axis.

17. The brace of claim 10 further comprising:
    a second plurality of slots in the structural layer that gives the brace a second limited axial rotation flexibility that is different than the first limited axial rotation flexibility.

18. The brace of claim 10 wherein the first plurality of slots are in a first region of the brace and a second plurality of slots are in a second region of the brace that is different than the first region of the brace.

* * * * *